US009861692B2

(12) United States Patent
Bett et al.

(10) Patent No.: US 9,861,692 B2
(45) Date of Patent: Jan. 9, 2018

(54) DENGUE VIRUS VACCINE COMPOSITIONS AND METHODS OF USE THEREOF

(71) Applicants: Andrew Bett, Lansdale, PA (US); Beth-Ann Griswold Coller, Kaneohe, HI (US); Govindarajan Dhanasekaran, Harleysville, PA (US); Ramesh V. Chintala, Chalfont, PA (US)

(72) Inventors: Andrew Bett, Lansdale, PA (US); Beth-Ann Griswold Coller, Kaneohe, HI (US); Govindarajan Dhanasekaran, Harleysville, PA (US); Ramesh V. Chintala, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/898,515

(22) PCT Filed: Jun. 17, 2014

(86) PCT No.: PCT/US2014/042625
§ 371 (c)(1),
(2) Date: Dec. 15, 2015

(87) PCT Pub. No.: WO2014/204892
PCT Pub. Date: Dec. 24, 2014

(65) Prior Publication Data
US 2016/0151477 A1 Jun. 2, 2016

Related U.S. Application Data

(60) Provisional application No. 61/837,721, filed on Jun. 21, 2013.

(51) Int. Cl.
| | |
|---|---|
| A61K 39/12 | (2006.01) |
| A61K 39/00 | (2006.01) |
| C12N 7/00 | (2006.01) |
| C07K 14/005 | (2006.01) |
| C12N 15/86 | (2006.01) |

(52) U.S. Cl.
CPC ...... *A61K 39/12* (2013.01); *A61K 2039/5254* (2013.01); *A61K 2039/545* (2013.01); *A61K 2039/55577* (2013.01); *A61K 2039/70* (2013.01); *C07K 14/005* (2013.01); *C12N 7/00* (2013.01); *C12N 15/86* (2013.01)

(58) Field of Classification Search
CPC .......... A61K 39/39; A61K 2039/55505; A61K 2039/55511; A61K 39/12; A61K 2039/5252; A61K 2039/6075; A61K 2039/525; A61K 2039/52524; C07K 14/005; C12N 7/00; C12N 15/1131; C12N 15/86; C12N 2770/24122; C12N 2770/24134; C12N 2770/24151
See application file for complete search history.

(56) References Cited

U.S. PATENT DOCUMENTS

| | | | |
|---|---|---|---|
| 6,190,859 B1 | 2/2001 | Putnak et al. | |
| 6,254,873 B1 | 7/2001 | Putnak et al. | |
| 6,432,411 B1 | 8/2002 | Ivy et al. | |
| 6,749,857 B1 | 6/2004 | Peters et al. | |
| 7,189,403 B2 | 3/2007 | Despres et al. | |
| 9,198,964 B2* | 12/2015 | Coller ............... | A61K 39/12 |
| 2007/0087015 A1 | 4/2007 | Eckels, II et al. | |
| 2009/0258036 A1 | 10/2009 | Whitehead et al. | |
| 2010/0230612 A1 | 9/2010 | Guy et al. | |
| 2012/0251570 A1 | 10/2012 | Alves et al. | |
| 2013/0095136 A1 | 4/2013 | Guirakhoo | |
| 2013/0216575 A1* | 8/2013 | Coller ............... | A61K 39/12 |
| | | | 424/218.1 |

FOREIGN PATENT DOCUMENTS

| | | |
|---|---|---|
| WO | WO96/40933 A1 | 12/1996 |
| WO | WO98/37911 A1 | 9/1998 |
| WO | WO2000/014245 A1 | 3/2000 |
| WO | WO2000/057907 A2 | 10/2000 |
| WO | WO2000/057908 A2 | 10/2000 |
| WO | WO2000/057909 A2 | 10/2000 |
| WO | WO2000/057910 A1 | 10/2000 |
| WO | WO02/095075 A1 | 11/2002 |
| WO | WO03/092592 A2 | 11/2003 |
| WO | WO2003/103571 A2 | 12/2003 |

(Continued)

OTHER PUBLICATIONS

Simmons M, Burgess T, Lynch J, Putnak R. Protection against dengue virus by non-replicating and live attenuated vaccines used together in a prime boost vaccination strategy. Virology. Jan. 20, 2010;396(2):280-8. Epub Nov. 13, 2009.*

Bray, Michael, et al.; "Construction of intertypic chimeric dengue viruses by substitution of structural protein genes"; Proc. Natl. Acad. Sci. USA; 1991; 10342-10346; 88.

(Continued)

*Primary Examiner* — Rachel B Gill
(74) *Attorney, Agent, or Firm* — Letitia Walker; Gloria M. Fuentes

(57) ABSTRACT

The present invention relates to dengue virus vaccine compositions comprising a first and a second dengue vaccine, wherein the first dengue vaccine is a live, attenuated dengue vaccine and the second dengue vaccine is a recombinant dengue subunit vaccine or an inactivated dengue vaccine; wherein the live attenuated dengue vaccine comprises at least one live, attenuated dengue virus or at least one live attenuated chimeric flavivirus. The dengue virus vaccine compositions of the invention may further comprise one or more adjuvants. In preferred embodiments of the invention, the first and the second dengue vaccine are tetravalent. The invention also relates to methods of using the dengue virus vaccine compositions of the invention to treat or prevent dengue infection, or to prevent, ameliorate, or delay the onset or progression of the clinical manifestations thereof.

18 Claims, 7 Drawing Sheets

(56) References Cited

FOREIGN PATENT DOCUMENTS

| | | |
|---|---|---|
| WO | WO2006/044857 A2 | 4/2006 |
| WO | WO2006/134433 A1 | 12/2006 |
| WO | WO2006134443 A1 | 12/2006 |
| WO | WO2007/002470 A2 | 1/2007 |
| WO | WO2007/015783 A2 | 2/2007 |
| WO | WO2007/141259 A1 | 12/2007 |
| WO | WO2008/022196 A2 | 2/2008 |
| WO | WO2008/047023 A2 | 4/2008 |
| WO | WO2008/127307 A2 | 10/2008 |
| WO | WO2012/154202 A1 | 11/2012 |
| WO | WO2014016362 | 1/2014 |

OTHER PUBLICATIONS

Bray, Michael, et al.; "Monkeys Immunized with Intertypic Chimeric Dengue Viruses Are Protected against Wild-Type Virus Challenge"; Journal of Virology; 1996; 4162-4166; 70(6).

Chen, Weiran, et al.; "Construction of Intertypic Chimeric Dengue Viruses Exhibiting Type 3 Antigenicity and Neurovirulence for Mice"; Journal of Virology; 1995; 5186-5190; 69(8).

Cuzzubbo, Andrea J., et al.; "Use of Recombinant Envelope Proteins for Serological Diagnosis of Dengue Virus Infection in an Immunochromatographic Assay"; Clinical and Diagnostic Laboratory Immunology; 2001; 1150-1155; 8(6).

Guirakhoo, F., et al.; "Recombinant Chimeric Yellow Fever-Dengue Type 2 Virus is Immunogenic and Protective in Nonhuman Primates"; Journal of Virology; 2000; 5477-5485; 74(12).

Guthrie, Alan J., et al.; "Protective immunication of horses with a recombinant canarypox virus vectored vaccine co-expressing genes encoding the outer capsid proteins of African horse sickness virus"; Vaccine; 2009; 4434-4438; 27.

Guy, Bruno, et al.; "Preclinical and clinical development of YFV 17D-based chimeric vaccines against dengue, West Nile and Japaese encephalitis viruses"; Vaccine; 2010; 632-649; 28.

Heinz, Franz X., et al.; "Flaviviruses and flavivirus vaccines"; Vaccine; 2012; 4301-4306; 30.

Lai, Ching-Juh, et al.; "Chimeric Flaviviruses: novel vaccines against dengue fever, tick-borne encephalitis, and japanese encephalitis"; Advances in Virus Research; 2003; 469-509; 61.

Lai, C.J., et al.; "Evaluation of molecular strategies to develop a live dengue vaccine"; Clinical and Diagnostic Virology; 1998; 173-179; 10.

Minke, J.M., et al.; "Protection provided by a recombinant ALVAC-WNV vaccine expressing the prM/E genes of a lineage 1 strain of WNV against a virulent challenge with a lineage 2 strain"; Vaccine; 2011; 4608-4612; 29.

Minke, J.M., et al.; "Use of DNA and recombinant canarypox viral (ALVAC) vectors for equine herpes virus vaccination"; Veterinary Immunology and Immunopathology; 2006; 47-57; 111.

Modis, Yorgo, et al.; "A ligand-binding pocket in the dengue virus envelope glycoprotein"; Proc. Natl. Acad. Sci. USA; 2003; 6986-6991; 100(12).

Modis, Yorgo, et al.; "Structure of the dengue virus envelope protein after membrane fusion"; Nature; 2004; 313-319; 427.

Monath, Thomas P., et al.; "A live, attenuated recombinant West Nile virus vaccine"; Proc. Natl. Acad. Sci. USA; 2006; 6694-6699; 103(17).

Putnak, Robert, et al.; "Development of a purified, inactivated, dengue-2 vaccine prototype in vero cells: immunogenicity and protection in mice and rhesus monkeys"; The Journal of Infectious Diseases; 1996; 1176-1184; 174.

Putnak, Robert J., et al.; "An evaluation of dengue type-2 inactivated, recombinant subunit, and live-attenuated vaccine candidates in the rhesus macaque model"; Vaccine; 2005; 4-442-4452; 23.

Simmons, Monika, et al.; "Protection against dengue virus by non-replicating and live attenuated vaccines used together in a prime boost vaccination strategy"; Virology; 2010; 280-288; 396.

Zhang, Ying, et al.; "Conformational Changes of the Flavivirus E Glycoprotein"; Structure; 2004; 1607-1618; 12.

Jutnak, J.R. et al., An evaluation of dengue type-2 inactivated, recombinant subunit, and live-attenuated vaccine candidates in the rhesus macaque model, Vaccine, Aug. 15, 2005, vol. 23, No. 35, pp. 4442-4452.

* cited by examiner

FIG. 4

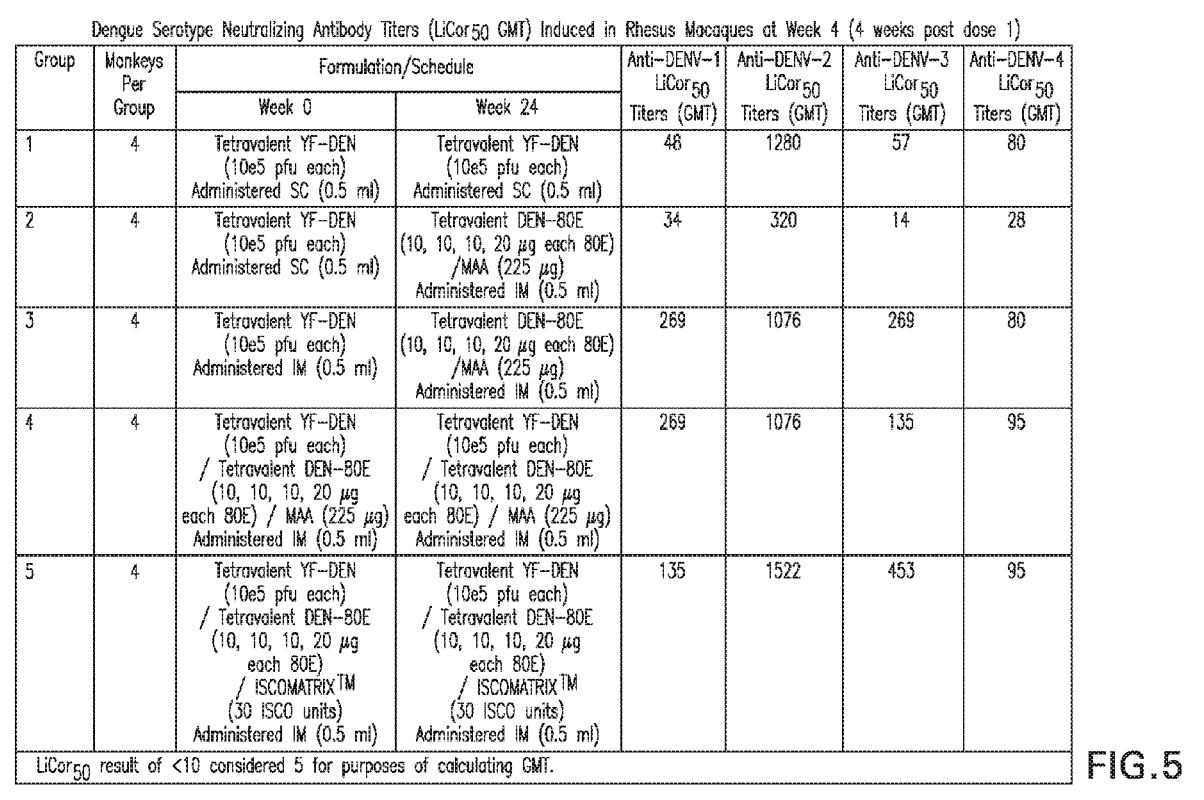

Dengue Serotype Neutralizing Antibody Titers (LiCor50 GMT) Induced in Rhesus Macaques at Week 4 (4

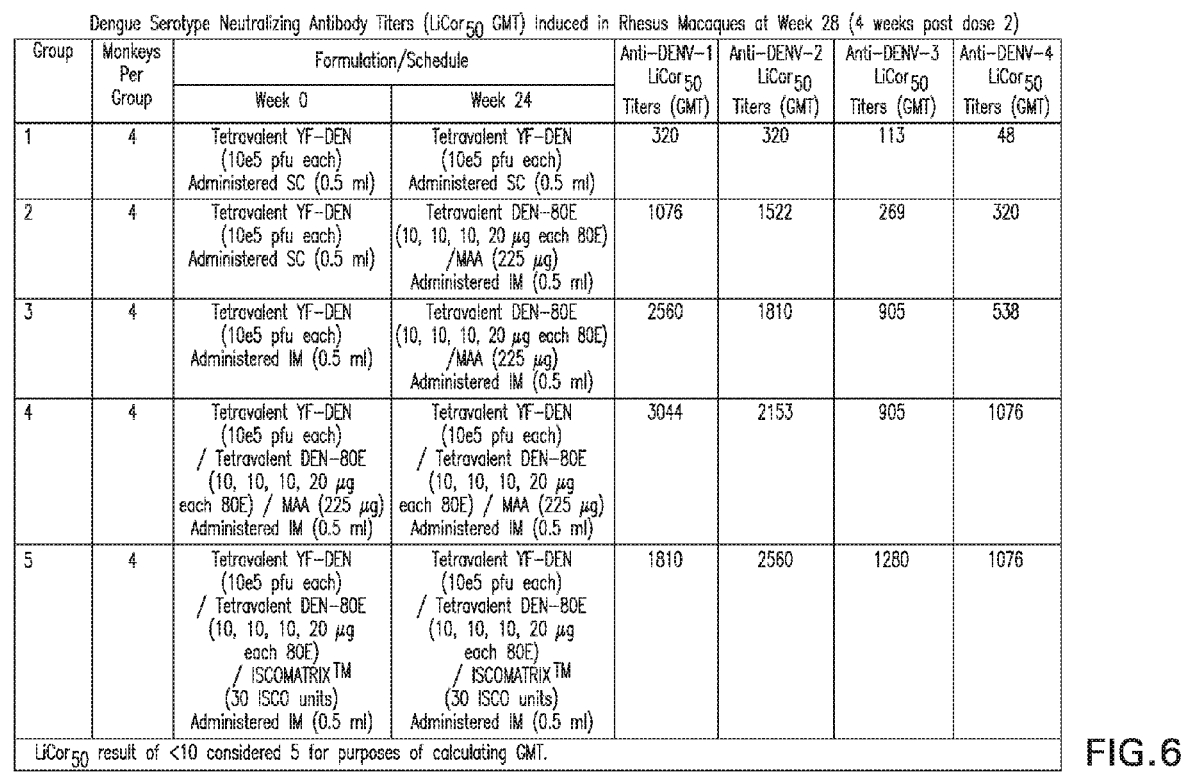

Dengue Serotype Neutralizing Antibody Titers (LiCor$_{50}$ GMT) Induced in Rhesus Macaques at

SEQUENCE LISTING

```
<160> NUMBER OF SEQ ID NOS: 5

<210> SEQ ID NO 1
<211> LENGTH: 395
<212> TYPE: PRT
<213> ORGANISM: Dengue 1

<400> SEQUENCE: 1

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190
```

```
Phe Asn Glu Met Val Leu Leu Thr Met Lys Glu Lys Ser Trp Leu Val
            195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
                275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Ser Thr Gln Asp Glu Arg Gly Val Thr Gln Asn Gly Arg Leu Ile
                340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Ile Gly Ala Gly Glu
            370                 375                 380

Lys Ala Leu Lys Leu Ser Trp Phe Lys Lys Gly
385                 390                 395

<210> SEQ ID NO 2
<211> LENGTH: 395
<212> TYPE: PRT
<213> ORGANISM: Dengue 2

<400> SEQUENCE: 2

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
    50                  55                  60

Leu Thr Asn Thr Thr Thr Asp Ser Arg Cys Pro Thr Gln Gly Glu Pro
65                  70                  75                  80

Thr Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
                100                 105                 110

Ile Val Thr Cys Ala Met Phe Thr Cys Lys Lys Asn Met Glu Gly Lys
            115                 120                 125

Ile Val Gln Pro Glu Asn Leu Glu Tyr Thr Val Ile Thr Pro His
    130                 135                 140

Ser Gly Glu Glu His Ala Val Gly Asn Asp Thr Gly Lys His Gly Lys
145                 150                 155                 160

Glu Val Lys Ile Thr Pro Gln Ser Ser Ile Thr Glu Ala Glu Leu Thr
                165                 170                 175
```

-continued

```
Gly Tyr Gly Thr Val Thr Met Glu Cys Ser Pro Arg Thr Gly Leu Asp
            180                 185                 190

Phe Asn Glu Met Val Leu Leu Gln Met Lys Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Gly Val Glu Pro
    370                 375                 380

Gly Gln Leu Lys Leu Asp Trp Phe Lys Lys Gly
385                 390                 395

<210> SEQ ID NO 3
<211> LENGTH: 393
<212> TYPE: PRT
<213> ORGANISM: Dengue 3

<400> SEQUENCE: 3

Met Arg Cys Val Gly Val Gly Asn Arg Asp Phe Val Glu Gly Leu Ser
1               5                   10                  15

Gly Ala Thr Trp Val Asp Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
        115                 120                 125

Val Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160
```

Glu Ile Thr Pro Gln Ala Ser Thr Val Glu Ala Ile Leu Pro Glu Tyr
            165                 170                 175

Gly Thr Leu Gly Leu Glu Cys Ser Pro Arg Thr Gly Leu Asp Phe Asn
        180                 185                 190

Glu Met Ile Leu Leu Thr Met Lys Asn Lys Ala Trp Met Val His Arg
        195                 200                 205

Gln Trp Phe Asp Leu Pro Leu Pro Trp Thr Ser Gly Ala Thr Thr
        210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
            245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
            275                 280                 285

Lys Leu Glu Leu Lys Gly Met Ser Tyr Ala Met Cys Leu Asn Thr Phe
        290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
            325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
            355                 360                 365

Pro Pro Phe Gly Glu Ser Asn Ile Val Ile Gly Ile Gly Asp Lys Ala
        370                 375                 380

Leu Lys Ile Asn Trp Tyr Lys Lys Gly
385                 390

<210> SEQ ID NO 4
<211> LENGTH: 395
<212> TYPE: PRT
<213> ORGANISM: Dengue 4

<400> SEQUENCE: 4

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
            85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Thr Val His
        130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
            165                 170                 175

Asp Tyr Gly Glu Leu Thr Leu Asp Cys Glu Pro Arg Ser Gly Ile Asp
        180                 185                 190

Phe Asn Glu Met Ile Leu Met Lys Met Lys Lys Thr Trp Leu Val
    195                 200                 205

His Lys Gln Trp Phe Leu Asp Leu Pro Leu Pro Trp Ala Ala Gly Ala
210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Thr Gly Ala Thr Glu Val Asp Ser
            260                 265                 270

Gly Asp Gly Asn His Met Tyr Ala Gly His Leu Lys Cys Lys Val Arg
        275                 280                 285

Met Glu Lys Leu Arg Ile Lys Gly Met Ser Tyr Thr Met Cys Ser Gly
290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Phe Ala Glu Tyr Thr Asn Ser Val Thr Asn Ile Glu
        355                 360                 365

Leu Glu Pro Pro Phe Gly Asp Ser Tyr Ile Val Ile Gly Val Gly Asp
370                 375                 380

Ser Ala Leu Thr Leu His Trp Phe Arg Lys Gly
385                 390                 395

<210> SEQ ID NO 5
<211> LENGTH: 451
<212> TYPE: PRT
<213> ORGANISM: Artificial Sequence
<220> FEATURE:
<223> OTHER INFORMATION: DEN4-80EZip

<400> SEQUENCE: 5

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

-continued

```
Val Val Thr Cys Ala Lys Phe Ser Cys Ser Gly Lys Ile Thr Gly Asn
            115                 120                 125

Leu Val Gln Ile Glu Asn Leu Glu Tyr Thr Val Val Thr Val His
            130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
            195                 200                 205

His Lys Gln Trp Phe Leu Asp Leu Pro Leu Pro Trp Ala Ala Gly Ala
            210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Thr Gly Ala Thr Glu Val Asp Ser
                260                 265                 270

Gly Asp Gly Asn His Met Tyr Ala Gly His Leu Lys Cys Lys Val Arg
            275                 280                 285

Met Glu Lys Leu Arg Ile Lys Gly Met Ser Tyr Thr Met Cys Ser Gly
            290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
                340                 345                 350

Ser Ser Thr Pro Phe Ala Glu Tyr Thr Asn Ser Val Thr Asn Ile Glu
            355                 360                 365

Leu Glu Pro Pro Phe Gly Asp Ser Tyr Ile Val Ile Gly Val Gly Asp
370                 375                 380

Ser Ala Leu Thr Leu His Trp Phe Arg Lys Gly Gly Gly Ser Gly
385                 390                 395                 400

Gly Gly Gly Thr Gly Gly Ser Gly Gly Gly Ser Pro Arg Met Lys
                405                 410                 415

Gln Leu Glu Asp Lys Val Glu Glu Leu Leu Ser Lys Asn Tyr His Leu
            420                 425                 430

Glu Asn Glu Val Ala Arg Leu Lys Lys Leu Val Gly Glu Arg Gly Gly
            435                 440                 445

Cys Gly Gly
        450
```

DENGUE VIRUS VACCINE COMPOSITIONS AND METHODS OF USE THEREOF

CROSS-REFERENCE TO RELATED APPLICATIONS

This application is a §371 National Stage Application of PCT/US2014/042625, having an international filing date of Jun. 17, 2014, which claims the benefit of U.S. Provisional Application No. 61/837,721, filed Jun. 21, 2013, the contents of which are herein incorporated by reference in their entirety.

FIELD OF THE INVENTION

The invention relates to compositions that elicit an immunological response against dengue virus infections, useful for the prevention and/or treatment of dengue virus infections in a subject, and/or the clinical manifestations thereof.

REFERENCE TO SEQUENCE LISTING SUBMITTED ELECTRONICALLY

The sequence listing of the present application is submitted electronically via EFS-Web as an ASCII formatted sequence listing with a file name "23532USPCT-SEQLIST-14DEC2015.TXT", creation date of Dec. 14, 2015, and a size of 154 KB. This sequence listing submitted via EFS-Web is part of the specification and is herein incorporated by reference in its entirety.

BACKGROUND OF THE INVENTION

The family Flaviviridae includes the prototype yellow fever virus (YF), the four serotypes of dengue virus (DEN-1, DEN-2, DEN-3, and DEN-4), Japanese encephalitis virus (JE), tick-borne encephalitis virus (TBE), West Nile virus (WN), Saint Louis encephalitis virus (SLE), and about 70 other disease causing viruses. Flaviviruses are small, enveloped viruses containing a single, positive-strand RNA genome. Ten gene products are encoded by a single open reading frame and are translated as a polyprotein organized in the order: capsid (C), "preMembrane" (prM, which is processed to "Membrane" (M) just prior to virion release from the cell), "envelope" (E), followed by non-structural (NS) proteins NS1, NS2a, NS2b, NS3, NS4a, NS4b and NS5 (reviewed in Chambers, T. J. et al., *Annual Rev Microbiol* (1990) 44:649-688; Henchal, E. A. and Putnak, J. R., *Clin Microbiol Rev.* (1990) 3:376-396). Individual flaviviral proteins are then produced through precise processing events mediated by host as well as virally encoded proteases.

The envelope of flaviviruses is derived from the host cell membrane and contains the virally-encoded membrane anchored membrane (M) and envelope (E) glycoproteins. The E glycoprotein is the largest viral structural protein and contains functional domains responsible for cell surface attachment and intra-endosomal fusion activities. It is also a major target of the host immune system, inducing the production of virus neutralizing antibodies, which are associated with protective immunity.

Dengue viruses are transmitted to man by mosquitoes of the genus *Aedes*, primarily *A. aegypti* and *A. albopictus*. Infection by dengue viruses leads to a diverse clinical picture ranging from an inapparent or mild febrile illness, through classical dengue fever (DF), to dengue hemorrhagic fever/dengue shock syndrome (DHF/DSS). Dengue fever is characterized by high fever, headache, joint and muscle pain, rash, lymphadenopathy and leucopenia (Gibbons, R. V. and D. W. Vaughn, *British Medical Journal* (2002) 324: 1563-1566). DHF/DSS is a more severe form of infection more common in children, marked by vascular permeability and/or severe hemorrhagic manifestations ranging from the presence of petechiae and ecchymosis to spontaneous severe hemorrhage and profound shock. Without diagnosis and prompt medical intervention, the sudden onset and rapid progression of DHF/DSS can be fatal if untreated.

Dengue viruses are the most significant group of arthropod-transmitted viruses in terms of global morbidity and mortality with an estimated one hundred million dengue infections occurring annually including at least 36 million cases of dengue fever and 250,000 to 500,000 cases of DHF/DSS (Gubler, D. J., *Clin. Microbiol. Rev.* (1998) 11:480-496; Gibbons, supra). With the global increase in population, urbanization of the population especially throughout the tropics, and the lack of sustained mosquito control measures, the mosquito vectors of dengue have expanded their distribution throughout the tropics, subtropics, and some temperate areas, bringing the risk of dengue infection to over half the world's population. Modern jet travel and human emigration have facilitated global distribution of dengue serotypes, such that multiple serotypes of dengue are now endemic in many regions. There has been an increase in the frequency of dengue epidemics and the incidence of DHF/DSS in the last 20 or more years. For example, in Southeast Asia, DHF/DSS is a leading cause of hospitalization and death among children (Gubler, supra; Gibbons and Vaughn, supra).

To date, the development of flavivirus vaccines has been met with mixed success. There are four basic approaches that have been implemented in an effort to produce vaccine candidates to protect against disease caused by flaviviruses: live-attenuated, inactivated whole virus, recombinant subunit protein, and DNA-based vaccines. A live-attenuated vaccine for yellow fever virus has been available for decades and more recently a live attenuated vaccine for Japanese encephalitis has been registered in various countries around the world. The use of inactivated whole virus vaccines has been demonstrated for TBE and JE viruses with several registered products available. Heinz et al. Flavivirus and flavivirus vaccines. *Vaccine* 30: 4301-06 (2012).

Despite the successes of the YF, JE, and TBE vaccines highlighted above, the use of live-attenuated virus and inactivated virus methods to develop vaccines for dengue virus has been met with significant challenges. There are four serotypes of dengue virus (DEN1, DEN2, DEN3, and DEN4) and strains of each serotype are found circulating throughout the dengue endemic regions of the world. Natural infection confers long lasting immunity to the infecting serotype but not to other dengue serotypes. The more severe forms of the disease (DHF/DSS) occur most often after secondary dengue infection, when infection with one serotype of dengue virus is followed by a second infection with another serotype. The more frequent association of DHF and DSS with secondary dengue infection has been hypothesized to be due to non-neutralizing antibodies induced by infection with one virus type enhancing infectivity of a second dengue virus type (antibody-dependent enhancement—ADE).

To date, the majority of the vaccines tested clinically are live, attenuated vaccines. The use of non-replicating vaccine candidates is also being explored. For example, Ivy et al. (U.S. Pat. No. 6,432,411) disclose a tetravalent subunit vaccine comprising DEN1-4 80% E (equivalent to amino acids 1-395 of the DEN-2 envelope polypeptide) proteins. Ivy et al, supra, also report compositions comprising DEN 1-4 80% E and ISCOMATRIX® adjuvant. Coller et al. (WO 2012/154202) disclose tetravalent formulations comprising DEN1-4 80% E of DEN 1-4. Inactivated viruses may also be used as potential vaccine candidates or as components of an effective vaccine (Putnak et al. Vaccine 23: 4442-4452 (2005), U.S. Pat. Nos. 6,190,859, 6,254,873 and Sterner et al. WO 2007/002470).

However, despite all these efforts to develop a dengue vaccine, to date no dengue vaccine is currently registered. Thus, there remains a need for a stable, safe, and effective vaccine that can induce a protective immune response against dengue infection and/or dengue-related disease.

SUMMARY OF THE INVENTION

The present invention relates to a dengue virus vaccine composition comprising a live, attenuated dengue vaccine ("LAV") and a second dengue vaccine, wherein the second dengue vaccine is a non-replicating dengue vaccine. In some embodiments, the non-replicating dengue vaccine is selected from a recombinant dengue subunit vaccine, a DNA vaccine, a conjugate vaccine, or an inactivated dengue vaccine, wherein the live attenuated dengue vaccine comprises at least one live, attenuated dengue virus or a live, attenuated chimeric dengue virus. In further embodiments, the non-replicating vaccine is either a dengue subunit vaccine or an inactivated dengue vaccine. In some embodiments of the invention, the LAV is tetravalent (i.e. comprises live, attenuated dengue viruses from DEN 1-4, or chimeric live, attenuated dengue viruses from DEN1-4, or a combination thereof). In some embodiments of the invention, the second vaccine is a recombinant subunit vaccine which comprises at least one dengue envelope (E) protein or fragment thereof. In preferred embodiments of the invention, the dengue subunit vaccine is tetravalent and comprises truncated dengue E proteins which each consist of about 80% of the length of wild type E of DEN1, DEN2, DEN3 and DEN4, starting from amino acid residue 1 at its N-terminus. The presence of the second dengue vaccine in the same composition as the live attenuated vaccine was found not to significantly impact live virus viability, thereby permitting the live and non-replicating vaccine to be administered in the same formulation In additional preferred embodiments of the invention, the live attenuated dengue vaccine is tetravalent and comprises four chimeric flaviviruses; wherein each of the four chimeric flaviviruses comprises the prM and E proteins of a single dengue virus serotype and the capsid and non-structural proteins of a different flavivirus, wherein each of the chimeric flaviviruses are attenuated. In some embodiments of the invention, the capsid and nonstructural proteins of the four chimeric flaviviruses are from yellow fever virus. In alternative preferred embodiments, the capsid and nonstructural proteins of each of the four chimeric flaviviruses are from a different dengue serotype than the prM and E proteins.

The invention also relates to dengue virus vaccine compositions that comprise a live, attenuated dengue vaccine and a recombinant dengue subunit vaccine and an adjuvant. In some embodiments described herein, the adjuvant is an aluminum salt adjuvant. In alternative embodiments, the adjuvant is a saponin-based adjuvant or a toll-like receptor agonist adjuvant.

Other aspects of this invention include methods of preventing dengue infection, or preventing or ameliorating the symptoms thereof, comprising administering an effective amount of the dengue virus vaccine compositions of the invention to a subject. In additional embodiments of this aspect of the invention, the compositions are administered in a prime/boost regime, wherein a dose of the composition is administered to a patient, a predetermined amount of time is allowed to pass, and a second dose of the composition is administered to the patient a second time. Additional doses may optionally be administered to the patient after a predetermined amount of time has passed between each dose.

In additional embodiments, the invention relates to a method of inducing an immune response against dengue infection, thereby reducing the likelihood of dengue infection, comprising the steps of: (a) mixing a first vaccine comprising a live, attenuated, tetravalent dengue vaccine and a second vaccine comprising a recombinant tetravalent dengue subunit vaccine or an inactivated dengue vaccine; wherein the live, attenuated, tetravalent dengue vaccine comprises live attenuated dengue virus or live attenuated chimeric dengue virus of dengue serotypes 1-4; and wherein the recombinant tetravalent dengue subunit vaccine comprises dengue envelope (E) proteins of dengue serotypes 1-4 or fragments thereof, to form a dengue virus vaccine composition; (b) administering the dengue virus vaccine composition of step (a) after mixing to a patient in which an immune response against dengue is to be induced, thereby reducing the likelihood of dengue infection. In some embodiments of the method, the immune response prevents dengue infection or prevents or ameliorates the symptoms thereof. In additional embodiments of this aspect of the invention, a second dose of the composition is administered to the patient after a predetermined amount of time is allowed to pass. The first vaccine and the second vaccine of the second dose of the composition can be formulated in a single vial or in two separate vials and mixed together prior to administration to the patient.

The invention also relates to the use of the dengue virus vaccine compositions of the invention for the treatment or prophylaxis of disease associated with dengue infection, such as dengue fever, DSS or DHF.

As used throughout the specification and in the appended claims, the singular forms "a," "an," and "the" include the plural reference unless the context clearly dictates otherwise.

Reference to "or" indicates either or both possibilities unless the context clear dictates one of the indicated possibilities. In some cases, "and/or" was employed to highlight either or both possibilities.

As used throughout the specification and appended claims, the following definitions and abbreviations apply:

The term "live attenuated vaccine," also referred to as "LAV" herein, means a vaccine comprising an effective amount of at least one live attenuated dengue virus and/or chimeric dengue virus and a pharmaceutically acceptable carrier, wherein the ability of the virus to cause disease is reduced compared to wild-type dengue virus.

The term "chimeric flavivirus vaccine" refers to a vaccine comprising an effective amount of a virus containing prM and/or E proteins of a dengue virus serotype and the capsid and non-structural proteins of a second, different flavivirus and a pharmaceutically acceptable carrier. The second flavivirus can be a different dengue serotype or another flavivirus, such as yellow fever virus.

"Non-replicating vaccine" refers to a dengue virus vaccine for the prevention or treatment of dengue virus infection or the clinical symptoms thereof, selected from a recombinant subunit vaccine, an inactivated vaccine, a conjugate vaccine, or a DNA vaccine.

"Inactivated vaccine" refers to a vaccine comprising an effective amount of a killed or inactive whole dengue virus and a pharmaceutically acceptable carrier, wherein the virus is inactivated by any means, including with chemicals, heat or radiation. An inactivated vaccine has a low residual infectivity following inactivation, e.g. <5 plaque forming units (PFU's)/mL after inactivation. In preferred embodiments, there is very low amount of residual infectivity following inactivation, e.g. ≤0.4 PFU's/mL, ≤3 PFU's/mL, or ≤2 PFU's/mL, <1 PFU/mL, ≤0.5 PFU/mL, or ≤0.1 PFU/mL. The PFU's of a particular vaccine may be determined using, for example, by using a plaque assay, an immunostaining assay, or other method known in the art for detecting viral infectivity.

"Conjugate vaccine" refers to a vaccine comprising a dengue antigen covalently attached to a carrier protein.

A "DNA vaccine" is a vaccine comprising a sequence of nucleotides that encodes a dengue protein antigen, including dengue proteins, dengue protein fragments, and dengue fusion proteins, and variants thereof. DNA vaccines comprise a plasmid (e.g. a DNA or viral plasmid) comprising a sequence of nucleotides that encode an antigen of interest, operably linked to a promoter.

"Subunit vaccine" refers to a vaccine that includes one or more dengue antigen components, but not complete dengue viruses, such as dengue immunogenic epitopes, dengue proteins, dengue antigen fusion proteins, including fusions of different dengue serotype antigens, or dengue protein fragments. Subunit vaccines, as used herein, can be monovalent (comprise a single dengue antigen) or multivalent (comprise more than one antigen component). In preferred embodiments, the subunit vaccine is tetravalent.

The dengue virus vaccines used in the compositions of the invention should be effective in inducing a virus neutralizing antibody response to the homologous dengue viruses in human volunteers and have an acceptable safety profile for healthy and at-risk human subjects.

The term "treatment" refers to both therapeutic treatment and prophylactic or preventative measures. Individuals "in need of" treatment include those already with a dengue infection, whether or not manifesting any clinical symptoms, as well as those at risk of being infected with dengue. Treatment of a patient with the dengue vaccine compositions of the invention includes one or more of the following: inducing/increasing an immune response against dengue in the patient, inducing a virus neutralizing antibody response against one or more dengue viruses, preventing, ameliorating, abrogating, or reducing the likelihood of the clinical manifestations of dengue in patients who have been infected with dengue, preventing or reducing the likelihood of developing dengue fever, DHF, or DSS and/or other disease or complication associated with dengue infection, reducing the severity or duration of the clinical symptoms of dengue infection and/or other disease or complication associated with the dengue, and preventing or reducing the likelihood of dengue infection.

The term "therapeutically effective amount" or "effective amount" means sufficient vaccine composition is introduced to a patient to produce a desired effect, including, but not limited to: inducing/increasing an immune response against dengue in the patient, inducing/increasing a virus neutralizing antibody response against dengue in a patient, preventing or reducing the likelihood of dengue infection, preventing or reducing the likelihood of dengue recurrent infection, preventing, ameliorating or abrogating the clinical manifestations of dengue infection in patients who have been infected with dengue, preventing dengue fever, DHF and/or DSS, reducing the severity or duration of disease associated with dengue. One skilled in the art recognizes that this level may vary.

The term "immune response" refers to a cell-mediated (T-cell) immune response and/or an antibody (B-cell) response.

The term "patient" refers to any human being that is to receive the dengue vaccine/immunogenic compositions described herein, including both immunocompetent and immunocompromised individuals. As defined herein, a "patient" includes those already infected with dengue, either through natural infection or vaccination or those that may subsequently be exposed.

"MAA" means Merck aluminum adjuvant. MAA is an amorphous aluminum hydroxyphosphate sulfate adjuvant. The term "MAA" is used interchangeably herein with the term "amorphous aluminum hydroxyphosphate sulfate" or "AAHS."

An "ISCOM-like adjuvant" is an adjuvant comprising an immune stimulating complex (ISCOM), which is comprised of a saponin, cholesterol, and a phospholipid, which together form a characteristic caged-like particle, having a unique spherical, caged-like structure that contributes to its function (for review, see Barr and Mitchell, *Immunology and Cell Biology* 74: 8-25 (1996)). This term includes both ISCOM™ adjuvants, which are produced with an antigen and comprise antigen within the ISCOM™ particle and ISCOM™ matrix adjuvants, which are hollow ISCOM-type adjuvants that are produced without antigen. In preferred embodiments of the compositions and methods provided herein, the ISCOM-type adjuvant is an ISCOM™ matrix particle adjuvant, such as ISCOMATRIX™, which is manufactured without antigen (ISCOM™ and ISCOMATRIX™ are registered trademarks of CSL Limited, Parkville, Australia).

"V180" refers to a tetravalent subunit vaccine comprised of truncated envelope glycoproteins (DEN-80E) from each of the 4 dengue virus serotypes (Dengue Virus (DENV) 1, DENV2, DENV3, and DENV4). See Coller et al. WO 2012/154202.

The following abbreviations are used herein and have the following meanings: DEN (alternatively DENV) is dengue virus, h is hours, GMT is geometric mean titer, IM is intramuscular, IMX is Iscomatrix™, LAV is live attenuated virus, MAA is Merck aluminum adjuvant, MAPA is Merck aluminum phosphate adjuvant, PFU is plaque forming units, SC is subcutaneous, WNV is West Nile Virus, YF (alternatively YFV) is yellow fever virus, and wt is wild type.

FIG. 2 shows the effect of mixing adjuvants and/or dengue subunit vaccine with recombinant chimeric YF-DEN (1-4) viruses. Each of the four chimeric YF-DEN viruses was field-mixed with the appropriate concentrations of tetravalent DEN-80E or tetravalent DEN-80E+adjuvant and the mixture was titered for viable virus at 0 h and 24 h post field-mix (see Examples 3 and 4). The final concentration of the virus was $1\times10^5$ PFU/dose (i.e. $2\times10^5$ PFU/ml).

FIG. 3 provides compatibility/stability data of co-formulations comprising wild type dengue viruses in the presence of adjuvants and/or dengue antigens (tetravalent DEN-80E, V180). Antigen/adjuvant samples were prepared as described in Example 5 and were field-mixed with wt Dengue viruses. Virus viability was tested using an in vitro plaque assay on Vero cells at 0 hours (striped bars) and 24 hours (solid bars) post field-mix as described in Example 6. Virus titer (PFU/ml) is provided for each dengue virus (D1-D4).

Figure 4:
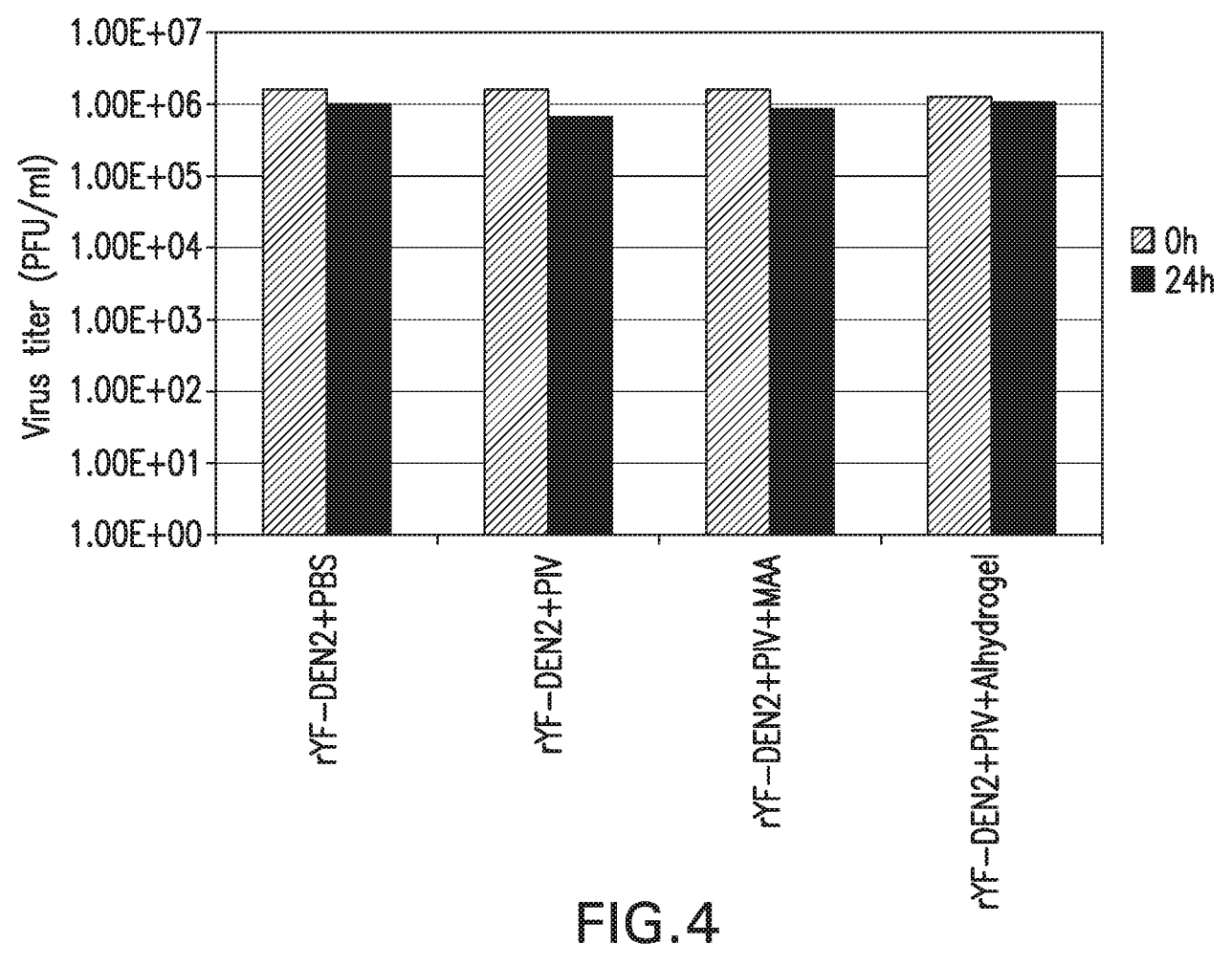

FIG. 4 provides compatibility/stability data of co-formulations comprising rYF-DEN2 chimeric live attenuated virus in the presence of adjuvants and/or dengue antigens (whole inactivated rYF-DEN2). Antigen/adjuvant samples were prepared as described in Example 7 and were field-mixed with rYF-DEN2 LAV, as described in Example 8. Virus viability was tested using an in vitro plaque assay on Vero cells at 0 hours (striped bars) and 24 hours (solid bars) post field-mix as described in Example 6. Virus titer (PFU/ml) is provided for mixtures of rYF-DEN2 LAV with: (1) PBS, (2) whole inactivated rYF-DEN2 ("PIV"), (3) PIV+MAA and (4) PIV+Alhydrogel.

FIG. 5 summarizes results of an immunogenicity study in rhesus macaques, which evaluated immunogenicity of co-formulations as part of a "prime-boost" vaccination strategy (groups 4 and 5) compared to a conventional prime boost strategy (groups 1-3). The co-formulations comprised a tetravalent recombinant dengue subunit vaccine candidate (V180) and a tetravalent dengue LAV. The geometric mean neutralization titers (LiCor 50 GMT) for DENV1, DENV2, DENV3 and DENV4 for all groups for Week 4 (4 weeks post dose 1) are provided. See Example 9.

FIG. 6 provides the geometric mean neutralization titers for DENV1, DENV2, DENV3 and DENV4 for the same groups shown in FIG. 5 for Week 28 (4 weeks post dose 2).

Figure 7:
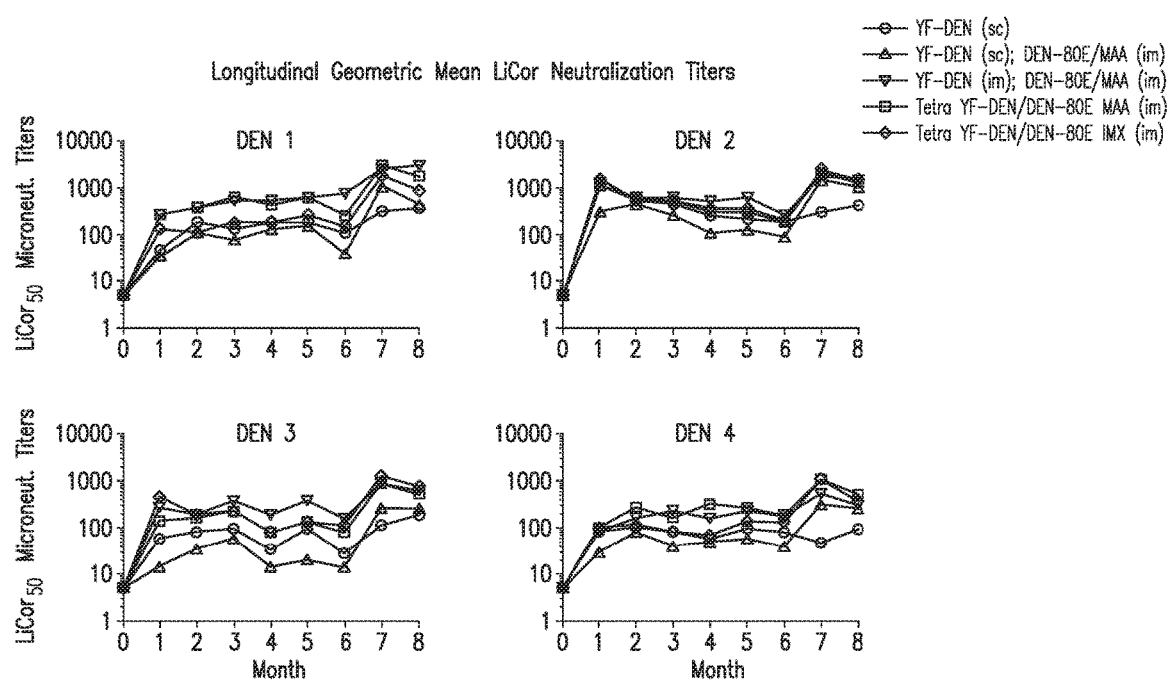

FIG. 7 shows the longitudinal geometric mean neutralization titers for DENV1, DENV2, DENV3 and DENV4 for groups described in Example 9.

DETAILED DESCRIPTION OF THE INVENTION

The invention relates to the co-formulation of a live attenuated dengue vaccine (LAV) with a second dengue vaccine, wherein the second dengue vaccine is a non-replicating dengue vaccine. In embodiments of the invention, the second vaccine is either a dengue subunit vaccine or an inactivated dengue vaccine, optionally further comprising an adjuvant. The LAV and the second vaccine are formulated in the same vial or separate vials and mixed together prior to administration to the subject. In embodiments of the invention, a composition in accordance with the invention is administered to a patient two or more times in a prime-boost treatment regime.

A conventional heterologous prime-boost regime comprising administration of the LAV at one point in time, followed by administration of the second dengue vaccine from 2 weeks to 2 years later is an alternative approach that can be used, but this approach may cause confusion regarding which vaccine (LAV or second vaccine) should be administered first in the series. Administration of the LAV and the second vaccine in the proper order is important because reversal of the order (subunit or inactivated vaccine first, followed by LAV) could lead to an inferior immune response which may increase the person's risk for more severe dengue disease if they were to become naturally infected. Thus, co-administration of the LAV and the second vaccine to a patient simplifies administration of the complete treatment regime. It is thought that, when administered in a prime-boost regime, the co-formulation of (1) LAV and (2) non-replicating vaccine will elicit strong immune responses that are primarily driven by the LAV at the prime and by the non-replicating vaccine at the boost.

Prior to the present invention, it was thought that the presence of subunit antigen or inactivated vaccine and/or adjuvant in a dengue vaccine composition comprising a live attenuated virus had the potential of inactivating the live attenuated virus resulting in decreased viral titer. Minke et al. (Vaccine 29 (2011) 46084612 and *Veterinary Immunol. and Immunopathol.* 111 (2006) 47-57) and Guthrie et al. (*Vaccine* 27 (2009) 4434-4438) reported a modified live recombinant canary pox virus expressing the prM/E genes derived from WNV formulated in carbomer adjuvant. However, this vaccine composition did not contain separate viral subunit antigens.

The use of different dengue virus vaccines in prime-boost strategies have been tested. Simmons et al. (*Virology* 396 280-288 (2010)) tested a prime boost approach for dengue in rhesus macaques by priming the animals with a non-replicating vaccine in the form of either an inactivated vaccine or a DNA-based vaccine, followed by boosting with a tetravalent live attenuated vaccine. Kanakatte et al. (WO 2008127307) also describe a heterologous prime boost regimen against dengue with the priming immunogen comprising a DNA expression system, an adenovirus expression vector or a Venezuelan equine encephalitis virus replicon system and the boosting immunogen comprising a tetravalent live attenuated vaccine. In this method, the boosting immunogen is administered between two weeks and 2 months of administration of the priming immunogen.

Guy et al. (WO 2008/047023) report a method for inducing protection against DEN1-4 in a patient, comprising: administering (a) a first series of administrations (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, and (b) a second series of administrations of doses (i) and (ii), in which the doses (i) and (ii) are administered simultaneously at separate anatomical sites, and in which the second series is implemented at least 30 days to at most 12 months after the first series. Thus previous reports of prime/boost approaches against dengue focus on the use of the LAV as the boosting immunogen and require that a period of time, from weeks to months passes between administration of the priming composition and administration of the LAV.

Figure 1:
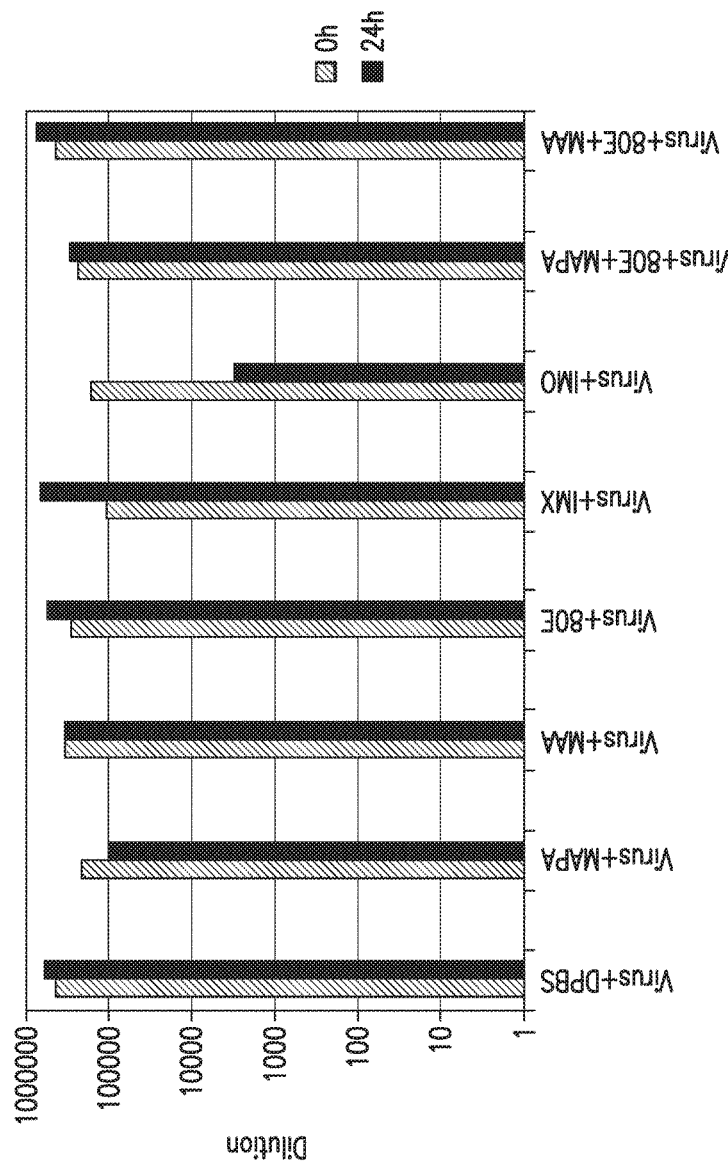
FIG. 1 shows the effect of field-mixing the listed adjuvants, antigen, or combinations with rYF-DEN2 LAV on virus titer at T=0 and T=24 hours post field-mix, as described in Examples 1 and 2. The final concentration of the virus was $1\times10^5$ PFU/dose (i.e. $2\times10^5$ PFU/ml).
Figure 2:
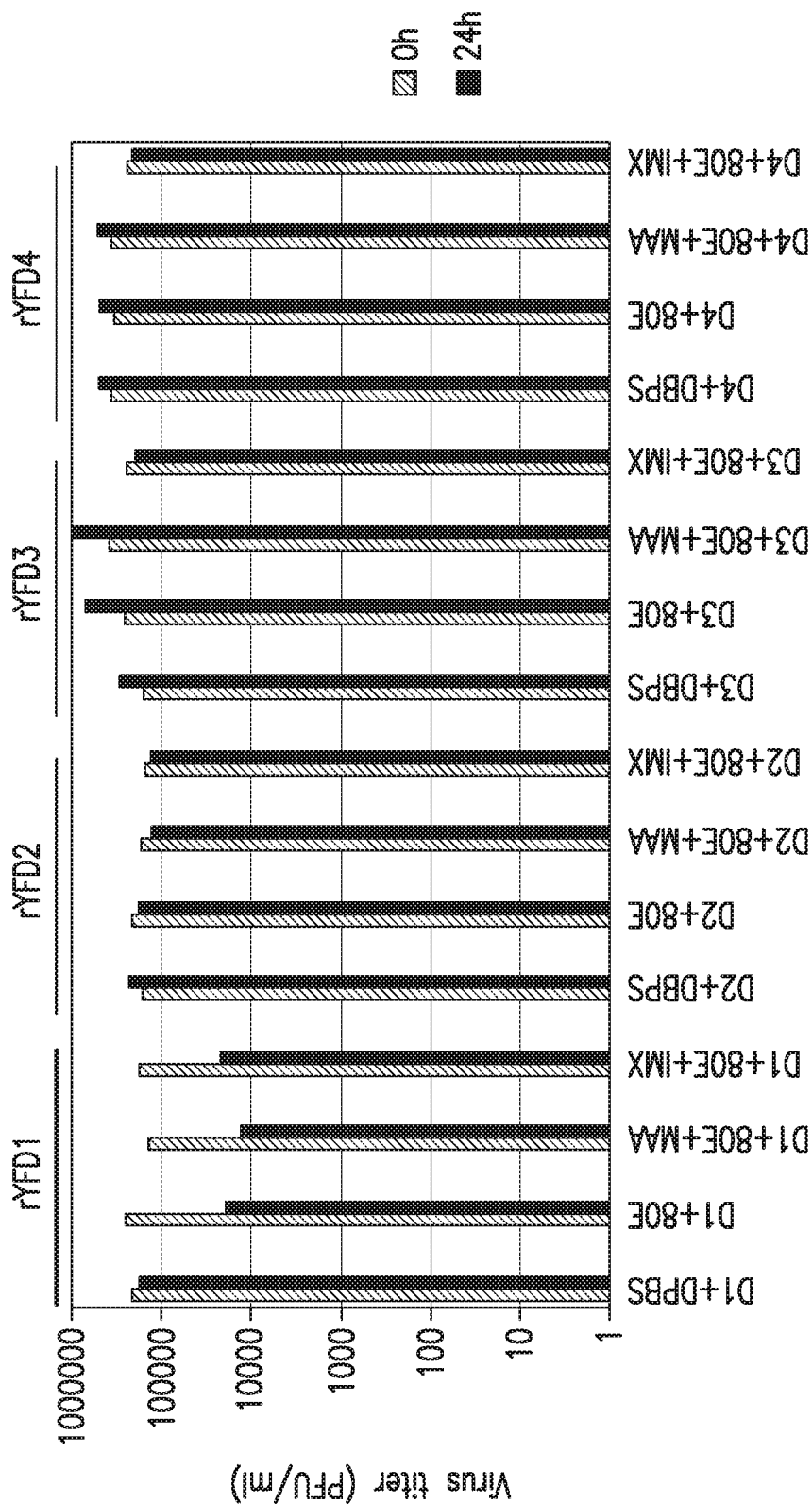

We have shown herein that, surprisingly, virus titer of live attenuated DEN viruses (monovalent and tetravalent chimeric rYF-DEN) were not significantly impacted by the addition of dengue subunit antigens (DEN2-80E or tetravalent DEN1-4 80E) and/or adjuvant in the same vial (see FIGS. 1 and 2, Examples 2 and 4), although a small reduction in the titer of DEN1 was observed upon addition of adjuvant after 24 hours. We have also shown that viability of wt dengue viruses was not impacted by formulation/mixture with dengue subunit antigens, either alone or mixed with MAA or Alhydrogel adjuvants (see FIG. 3 and Example 5). It was further shown that viral titer of chimeric rYF-DEN2 LAV was not impacted by mixture with whole inactivated rYF-DEN2, either alone or mixed with MAA or Alhydrogel adjuvants (FIG. 4, Examples 7-8).

It was further shown herein that the use of a conventional prime boost (tetravalent LAV prime, V180 subunit boost) and the co-formulation prime boost approaches (tetravalent LAV+tetravalent subunit co-formulation prime, followed by tetravalent LAV+tetravalent subunit co-formulation boost) induced superior neutralization titers to all four DENV types compared to a prime-boost regime using tetravalent YF- DEN LAV vaccine as both prime and boost (see Example 9, FIGS. 5 and 6). The neutralization responses measured in the co-formulation groups at four weeks post dose 2 were equivalent to those induced in the groups receiving the conventional prime-boost regimen. This indicates that the co-formulation of the YF-DEN vaccine with a tetravalent dengue subunit vaccine and adjuvants (MAA or ISCOMATRIX®) does not negatively impact the response to the subunit boost.

Thus, the benefits of a heterologous prime/boost approach may be achieved through administration of a co-formulation comprising: (1) a dengue LAV and (2) a second dengue vaccine, wherein the second dengue vaccine is a non-replicating dengue vaccine. In some embodiments of the invention, the non-replicating vaccine is selected from a subunit dengue vaccine and an inactivated dengue vaccine as both the priming and as the boosting composition.

Accordingly, the invention relates to a method of preventing or reducing the likelihood of dengue infection, or preventing, treating, or ameliorating the clinical manifestations thereof, the method comprising:

(a) administering a first dengue virus vaccine composition comprising a live attenuated dengue vaccine (LAV) and a second dengue vaccine to a patient in need thereof, wherein the second vaccine is a non-replicating dengue vaccine;

(b) waiting for a predetermined amount of time to pass after step (a); and (c) administering to the patient a second dengue virus vaccine composition comprising a dengue LAV and a second dengue vaccine, wherein the second dengue vaccine is a non-replicating dengue vaccine. In some embodiments of the method above, the non-replicating vaccine is a dengue subunit vaccine or an inactivated dengue vaccine.

In some embodiments, the second dengue virus vaccine composition (co-formulation) of step (c) is the same as the co-formulation (first dengue virus vaccine composition) of step (a). In alternative embodiments, the co-formulation of step (c) is not the same as the co-formulation of step (a). In additional embodiments, the method comprises repeating steps (b) and (c) one or more times. In some embodiments, the LAV and the second dengue vaccine of step (a) and/or step (c) are formulated in separate vials and mixed together prior to administration. It is thought that the use of the compositions of the invention in a prime/boost regime will elicit strong immune responses that are primarily driven by the LAV at the prime (first dose) and by the non-replicating (e.g. subunit or inactivated vaccine) at the boost (second dose).

Accordingly, the present invention relates to a dengue virus vaccine composition comprising effective amounts of a first dengue vaccine and a second dengue vaccine and a pharmaceutically acceptable carrier, wherein the first dengue vaccine is a live, attenuated dengue vaccine and the second dengue vaccine is a non-replicating dengue vaccine, wherein the live attenuated dengue vaccine comprises at least one live, attenuated dengue virus or at least one live attenuated chimeric flavivirus. In some embodiments of the invention, the non-replicating vaccine of the dengue virus vaccine compositions of the invention are selected from a recombinant dengue subunit vaccine or an inactivated dengue vaccine.

To prepare pharmaceutical or sterile dengue virus vaccine compositions of the invention, a first dengue vaccine and a second dengue vaccine are admixed with a pharmaceutically acceptable carrier or excipient. Alternatively, the first dengue vaccine and the second dengue vaccine comprise a pharmaceutically acceptable carrier prior to mixing and no additional carrier is required when the vaccines are mixed. See, e.g., Remington's *Pharmaceutical Sciences and U.S. Pharmacopeia: National Formulary*, Mack Publishing Company, Easton, Pa. (1984). Pharmaceutically acceptable carriers include any and all solvents, dispersion media, isotonic and absorption delaying agents, and the like that are physiologically compatible. The carriers can be suitable for intravenous, intramuscular, subcutaneous, parenteral, rectal, spinal, or epidermal administration (e.g., by injection or infusion).

As used herein, the term "pharmaceutically acceptable carrier" refers to a substance, as described above, which is admixed with an active ingredient (e.g. whole, inactivated virus, live attenuated virus, live attenuated chimeric virus, viral protein, plasmid comprising a sequence of nucleotides encoding a dengue antigen protein, or dengue antigen conjugate) of the invention that is suitable for administration to humans. In embodiments of the invention, the pharmaceutically acceptable carrier does not occur in nature in the same form, e.g. the substance is man-made, either because it does not exist in nature or the purity and/or sterility of the substance is not the same as the corresponding natural substance. For example, sterile water for injection, which is a sterile, bacteria-free, solute-free preparation of distilled water for injection, does not occur in nature in the same form and is considered a pharmaceutically acceptable carrier. In some embodiments, the pharmaceutical compositions of the invention comprise one or more active ingredients disclosed herein (e.g. a tetravalent LAV) and sterile water for injection. In further embodiments, the pharmaceutically acceptable carrier may be another form of water that is appropriate for pharmaceutical or biological preparations and is not the same as water that occurs in nature, including purified water, water for injection, sterile purified water, and bacteriostatic water for injection.

Pharmaceutical compositions typically should be sterile and stable under the conditions of manufacture and storage. Formulations of therapeutic and diagnostic agents may be prepared by mixing with acceptable carriers, excipients, or stabilizers in the form of, e.g., lyophilized powders, slurries, aqueous solutions, suspensions, microemulsions, dispersions, liposomes, or other ordered structure suitable for vaccine formulation and administration (see, e.g., Hardman, et al. (2001) Goodman and Gilman's *The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

The dengue virus vaccine compositions of the present invention may further comprise additional components including, but not limited to adjuvants, as discussed infra, buffers, stabilizers, solubilizers, salt, anti-microbial preservatives, surfactants, tonicity modifiers, chelating agents, dextran, dextran sulfate, dextran T40, diethanolamine, guanidine, calcium chloride, sodium citrate, albumin, gelatin, polyethylene glycol (PEG), lipids, and heparin. One of skill in the art is readily able to determine which additional excipients should be included in a desired dengue virus vaccine composition, dependent on its function in the formulation, as well as the projected mode of administration, dosage, and other factors such as the expected storage time and temperature of the composition. One of skill in the art recognizes that the amount of the additional excipients may vary, and can readily determine a proper amount that is both safe for administration to humans and effective for the desired function.

Live Attenuated Dengue Virus Vaccine

As stated above, the dengue virus vaccine compositions of the invention comprise a live attenuated dengue vaccine that: induced an immune response against dengue, induces a virus neutralizing antibody response against dengue, protects against or reducing the likelihood of infection or reduces the severity or duration of the clinical manifestations thereof, with at least one of dengue virus type 1 (DEN1), dengue virus type 2 (DEN2), dengue virus type 3 (DEN3) and dengue virus type 4 (DEN4). In embodiments of the invention, the live attenuated dengue vaccine is monovalent, bivalent, trivalent or tetravalent. In preferred embodiments of the invention, the LAV is tetravalent, i.e. protects against DEN types 1-4 and comprises a DEN1, a DEN2, a DEN3 and a DEN4 LAV component.

Each LAV component of the invention comprises a live, attenuated virus which is independently either an attenuated chimeric flavivirus or an attenuated dengue virus. Attenuation of the dengue virus can be achieved by different techniques, including methods known in the art such as through serial passage on tissue culture or through more defined genetic manipulations. Mutations useful for attenuating dengue viruses and chimeric dengue viruses are known in the art. See, e.g. WO 02/095075, WO 2006/44857, U.S. Pat. No. 7,189,403, WO 2003/103571, WO 2000/014245, and WO 2008/022196. Known attenuated dengue strains can also be used in the compositions herein, such as the strains described in WO 06/134433, WO 2006/134443, WO 2007/141259, WO 96/40933, WO 2000/057907, WO 2000/057908, WO 2000/057909, WO 2000/057910, and WO 2007/015783.

Preferred embodiments include a tetravalent live attenuated dengue vaccine. Such tetravalent live attenuated vaccine can comprise four attenuated dengue strains, three attenuated dengue strains and one attenuated chimeric flavivirus strain, two attenuated dengue strains and two attenuated chimeric flavivirus strains, one attenuated dengue strain and three attenuated chimeric flaviviruses, or four attenuated chimeric flaviviruses.

In embodiments of the invention comprising chimeric flaviviruses, each chimeric flavivirus comprises the prM and E proteins of a single dengue virus serotype and the capsid and non-structural proteins (i.e. "the backbone") of a different flavivirus, wherein each of the chimeric flaviviruses are attenuated. Methods for construction of a recombinant, live attenuated flavivirus strain may comprise the use of a known attenuated strain as a base, wherein the method comprises substituting the appropriate genes (prM and E) from a related virus of interest for the equivalent genes of the base virus. For example, this approach has been used for WNV wherein the chimeric virus is an intertypic chimeric based on an attenuated DEN-4 strain comprising prM and E genes of WNV (Bray, M. et al., *J. Virol.* (1996) 70:4162-4166; Chen, W., et al., *J. Virol.* (1995) 69:5186-5190; Bray, M. and Lai, C.-J., *Proc. Natl. Acad. Sci. USA* (1991) 88:10342-10346; Lai, C. J. et al., *Clin. Diagn. Virol.* (1998) 10:173-179).

Another approach has been the use of the YF 17D attenuated yellow fever strain as a base to develop recombinant chimeric vaccines, which was previously used for JE virus, DEN viruses, and WN virus. A chimeric yellow fever vaccine can be constructed comprising a yellow fever backbone by replacing the genes coding for prM and E proteins from any yellow fever strain, for example, YFV 17D, with those of a Dengue serotype. After DNA cloning, RNA is transcribed and transfected into Vero cells to obtain chimeric viruses possessing the YFV 17D replication machinery and the external coat of the relevant Dengue virus. See Guirakhoo et al., *Journal of Virology,* 74(12): 5477-5485 (2000); Guy et al., *Vaccine* 28: 632-649 (2010); Monath T. P. *Adv Virus Res* (2003) 61:469-509; Monath et al. *Proc. Natl. Acad. Sci. USA* (2006) 103:6694; and WO 98/37911. Thus, in some embodiments of the invention, the live attenuated vaccine comprises a chimeric flavivirus comprising the prM and E proteins of a single dengue serotype and a yellow fever backbone.

Chimeric live attenuated vaccines useful in the compositions of the invention may also comprise a dengue chimeric virus, wherein the prM and E proteins are of a single dengue virus serotype and the capsid and nonstructural proteins are of a different dengue virus serotype. In embodiments wherein the chimeric virus comprises a backbone from a second dengue serotype, any dengue backbone that is attenuated can be used in the chimeric virus. Attenuation can be achieved through serial passage, through the introduction of defined genetic mutations, or through the use of known attenuated dengue strains. Dengue chimeric vaccines are described, for example, in Whitehead et al. WO 03/092592. In some embodiments of the invention, the live attenuated vaccine comprises a chimeric flavivirus wherein the capsid and nonstructural proteins are from a different dengue serotype than the prM and E proteins.

The dengue virus vaccine compositions of the invention comprise an effective amount of live attenuated virus vaccine. In some embodiments of the invention, the potency of the live attenuated dengue vaccine is from 10 to about $1 \times 10^7$ plaque forming units (PFU's). In alternative embodiments, the potency of the live attenuated dengue vaccine is from about $1 \times 10^2$ to about $1 \times 10^6$ PFU's. In other embodiments, the potency of the live attenuated dengue vaccine is from about $1 \times 10^3$ to about $1 \times 10^5$ PFU's.

Dengue Subunit Vaccine

In some embodiments of the invention, the composition comprises a dengue subunit vaccine which comprises one or more dengue antigen proteins. In preferred embodiments of this aspect of the invention, the subunit vaccine comprises one or more dengue proteins, fusion proteins, or a fragment or fragments thereof. In further preferred embodiments, the dengue subunit vaccine comprises dengue envelope or E protein, or a fragment thereof.

In further preferred embodiments, the subunit vaccine is tetravalent, i.e. targets an immune response against all four dengue serotypes. A tetravalent subunit vaccine can comprise four recombinant dengue proteins or less than four, e.g. a recombinant DEN1 protein, a recombinant DEN2 protein, and a recombinant DEN3/4 fusion protein. In some embodiments, the subunit vaccine comprises dengue virus envelope glycoprotein, or fragments thereof, of DEN1-4 (e.g. DEN1-80E, DEN2-80E, DEN3-80E, DEN4-80E, or DEN4-80EZip) that is produced and secreted using a recombinant expression system. Said subunit vaccine may optionally comprise an adjuvant, as described more fully below.

In some embodiments of this aspect of the invention, the dengue subunit vaccine comprises one or more purified dengue virus envelope ("E") proteins, a pharmaceutically acceptable excipient, wherein the E proteins each constitute approximately 80% of the length of wild type E starting from amino acid residue 1 at its N-terminus, such that said E protein is secretable into growth medium when expressed recombinantly in a host cell and wherein the composition induces the production of neutralizing antibodies in human subjects. In some embodiments of the invention, the dengue subunit vaccine further comprises an effective amount of an adjuvant. In some embodiments of the invention, the DEN-4 E protein is dimeric ("DEN4-80EZip"), as described in U.S. Pat. No. 6,749,857 and WO 2012/154202.

In some embodiments of this aspect of the invention, the E proteins in the composition described above are recombinantly produced and expressed in insect host cells. In further preferred embodiments, the E protein is recombinantly produced and expressed in *Drosophila melanogaster* Schneider 2 (S2) host cells.

The recombinant subunit dengue virus E proteins of the present invention can be produced by means of a cell culture expression system that uses *Drosophila* Schneider 2 (S2) cells. This system has been demonstrated to produce dengue recombinant envelope proteins that maintain native-like structure (Cuzzubbo et al., *Clin. Diagn. Lab. Immunol.* (2001) 8:1150-55; Modis et al., *Proc. Natl. Acad. Sci.* (2003) 100:6986-91; Modis et al., *Nature* (2004) 427:313-9; Zhang et al., Structure (2004)12(9):1607-18). This expression system has also been shown to express other recombinant envelope proteins from other flaviviruses such as West Nile, Japanese Encephalitis, hepatitis C, and Tick Borne Encephalitis viruses. The recombinant envelope proteins may be truncated at the C-terminus, leaving 80% of the native envelope protein ("80E"). Thus 80E is defined as approximately the first 80% of consecutive amino acids of E protein starting at amino acid 1 of its N-terminus.

As stated above, some embodiments of this aspect of the invention comprise truncated 80E proteins which consist of approximately 80% of the length of wild type E starting from amino acid residue 1 at its N-terminus. The E proteins used in some embodiments of the invention delete the membrane anchor portion (approximately the last 10% of E at the carboxy end) of the protein, in other words, up to the first 90% of consecutive amino acids of E starting at amino acid 1 of its N-terminus, thus allowing it to be secreted into the extracellular medium, facilitating recovery. The truncation may further delete the "stem" portion of the E protein that links the 80E portion with the membrane anchor portion; the stem portion does not contain notable antigenic epitopes and therefore is not included in the preferred antigens, DEN1-80E, DEN2-80E, DEN3-80E, DEN4-80E, or DEN4-80EZip. More than 90%, but less than 100%, of the E protein can be cloned and secreted, i.e., the protein can be 90%+ in length, carboxy truncated, and can include a portion of the membrane spanning domain so long as the truncated E protein is secretable. "Secretable" means able to be secreted, and typically secreted, from the transformed cells in the expression system. Thus, one of skill in the art will realize that Dengue E proteins that are useful in the compositions and methods of the present invention may vary from the 80% exemplified herein, as long as the protein is secretable. In preferred embodiments of each aspect of the present invention, the DEN E proteins are about 80% in length starting from the N-terminal amino acid of the envelope protein and ending at an amino acid in the range of the $393^{rd}$ to $401^{st}$ amino acid, for example, from amino acid 1 to amino acid 395 of dengue virus type 2. In alternative embodiments of each aspect of the invention, the dengue E protein may be about 75%, about 85%, about 90%, about 95%, or about 98% of the consecutive amino acids of E starting at amino acid 1 of its N-terminus. In exemplary embodiments of aspects of the invention herein, the DEN E protein is approximately 80% of consecutive amino acids of E protein starting at amino acid 1 of its N-terminus; such as DEN1-80E, as set forth in SEQ ID NO:1, DEN2-80E, as set forth in SEQ ID NO:2, DEN3-80E, as set forth in SEQ ID NO:3 and DEN4-80E, as set forth in SEQ ID NO:4.

The secreted E protein may further contain domains which facilitate dimerization, such as in the DEN4-80EZip protein, such that the immunogenicity of the recombinant protein is further enhanced. An exemplary DEN4-80EZip protein comprises an amino acid sequence as set forth in SEQ ID NO:5. In some embodiments of this aspect of the invention, the DEN1, DEN2, and DEN3 80E antigens included in the composition are monomeric and the DEN4 80E antigen is dimeric.

In alternative embodiments of this aspect of the invention, the DEN1-80E, DEN2-80E, DEN3-80E and DEN4-80E proteins in the composition are monomeric. In such embodiments, the DEN4 component is present in an amount that is about 1.5 to about 3 times the individual amounts of DEN1, DEN2, and DEN3 proteins, preferably about 2 times the amount of the DEN1, DEN2, and DEN3 components (proteins). In preferred embodiments of this aspect of the invention, the ratio of DEN1:DEN2:DEN3:DEN4 antigens in the compositions is approximately 1:1:1:2.

In embodiments of the invention comprising dengue E proteins, the amount of each E protein in the composition is from about 0.5 µg to about 500 µg. In alternative embodiments, the amount of each E protein is from about 0.5 µg to about 450 µg, 0.5 µg to about 400 µg, 0.5 µg to about 350 µg, 0.5 µg to about 300 µg, 0.5 µg to about 250 µg, 0.5 µg to about 200 µg, 0.5 µg to about 150 µg, 0.5 µg to about 100 µg, 0.5 µg to about 50 µg, 5.0 µg to about 500 µg, 5.0 µg to about 450 µg, 5.0 µg to about 400 µg, 5.0 µg to about 350 µg, 5.0 µg to about 300 µg, 5.0 µg to about 250 µg, 5.0 µg to about 200 µg, 5.0 µg to about 150 µg, 5.0 µg to about 100 µg, 5.0 µg to about 50 µg, 10 µg to about 450 µg, 10 µg to about 450 µg, 10 µg to about 400 µg, 10 µg to about 350 µg, 10 µg to about 300 µg, 10 µg to about 250 µg, 10 µg to about 200 µg, 10 µg to about 150 µg, 10 µg to about 100 µg, 10 µg to about 50 µg, 25 µg to about 500 µg, 25 µg to about 450 µg, 25 µg to about 400 µg, 25 µg to about 350 µg, 25 µg to about 300 µg, 25 µg to about 250 µg, 25 µg to about 200 µg, 25 µg to about 150 µg, 25 µg to about 100 µg, or 25 µg to about 50 µg. In further preferred embodiments, the amount of each E protein in the composition is from about 1.0 µg to about 100 µg. In still further embodiments, the amount of each E protein in the composition is selected from approximately 10, 20, 30, 40, 50, 60, 70, 80, 90, 100, 150, 200, 250, 300, 350, 400, 450, or 500 µg.

Inactivated Dengue Vaccine

As an alternative to a dengue subunit vaccine in the dengue vaccine compositions of the invention, a whole inactivated dengue vaccine or inactivated dengue chimeric vaccine, may also be used. Inactivated dengue vaccines of the compositions herein comprise one or more whole inactivated dengue viruses and/or one or more inactivated chimeric viruses. In some embodiments of this aspect of the invention, the inactivated dengue vaccine is tetravalent and comprises whole inactivated DEN1, DEN2, DEN3 and DEN4. In alternative embodiments, the inactivated vaccine comprises four inactivated chimeric dengue viruses. In still other embodiments, the inactivated vaccine is tetravalent and comprises one or more whole inactivated dengue viruses and one or more inactivated dengue chimeric viruses, e.g. an inactivated whole DEN1 virus, an inactivated whole DEN2 virus, an inactivated DEN3 chimeric virus and an inactivated DEN4 chimeric virus. One of skill in the art realizes that any combination of inactivated whole or chimeric DEN viruses may be used in the tetravalent compositions and methods of the invention, as long as the vaccine composition targets all four dengue serotypes.

Inactivated dengue vaccines useful in the compositions and methods of the invention are described in Putnak et al. Vaccine 23: 4442-4452 (2005), U.S. Pat. Nos. 6,190,859, 6,254,873 and Sterner et al. WO 2007/002470. Alternatively, dengue virus strains and chimeric dengue strains/chimeric flavivirus strains can be inactivated for use in the compositions and methods of the invention through methods known in the art, e.g., with chemicals, heat or radiation.

Adjuvants

Co-administration of vaccines with compounds that can enhance the immune response against the antigen of interest, known as adjuvants, has been extensively studied. In addition to increasing the immune response against the antigen of interest, some adjuvants may be used to decrease the amount of antigen necessary to provoke the desired immune response or decrease the number of injections needed in a clinical regimen to induce a durable immune response and provide protection from disease.

To that end, the invention relates to dengue virus vaccine compositions of the invention may employ an adjuvant. The adjuvant of the compositions described herein can be any adjuvant that performs the desired function, as described above, and does not inactivate or significantly impact the titer of the LAV of the composition.

Aluminum-based compounds were determined to possess adjuvant activity over 60 years ago (for review, see Lindblad, E. B. Immunol. and Cell Biol. 82: 497-505 (2004); Baylor et al. Vaccine 20: S18-S23 (2002)). Aluminum adjuvants are generally regarded as safe when used at appropriate dosages. Many have been approved for administration into humans by regulatory agencies worldwide.

Accordingly, aluminum-based compounds, such as aluminum hydroxide ($Al(OH)_3$), aluminum hydroxyphosphate ($AlPO_4$), amorphous aluminum hydroxyphosphate sulfate (AAHS), or so-called "alum" ($KAl(SO_4).12H_2O$) (see Klein et al., Analysis of aluminum hydroxyphosphate vaccine adjuvants by Al MAS NMR., J. Pharm. Sci. 89(3): 311-21 (2000)), may be combined with the compositions provided herein. In exemplary embodiments of the invention provided herein, the aluminum adjuvant is aluminum hydroxyphosphate or AAHS, alternatively referred to as "MAA". In alternative embodiments, the aluminum adjuvant is an aluminum phosphate adjuvant, referred to herein as "MAPA". In other embodiments, the adjuvant is aluminum hydroxide.

One of skill in the art will be able to determine an optimal dosage of aluminum adjuvant that is both safe and effective at increasing the immune response to the targeted dengue viruses. For a discussion of the safety profile of aluminum, as well as amounts of aluminum included in FDA-licensed vaccines, see Baylor et al., Vaccine 20: S18-S23 (2002). Generally, an effective and safe dose of aluminum adjuvant varies from 50 µg to 1.25 mg elemental aluminum per dose (100 µg/mL to 2.5 mg/mL concentration).

Thus, specific embodiments of the present invention include compositions comprising a live attenuated dengue virus vaccine and a second dengue vaccine, wherein the second vaccine is a non-replicating vaccine, as described in any embodiment herein, and further comprising an aluminum adjuvant. In some embodiments, the non-replicating vaccine is selected from a dengue subunit vaccine or an inactivated dengue vaccine. In embodiments of the invention, the dengue compositions comprise an adjuvant which comprises from about 50 µg to about 1.25 mg of elemental aluminum per dose of vaccine. In other embodiments, the aluminum adjuvant per dose of vaccine composition comprises an amount of elemental aluminum ranging from about 100 µg to about 1.0 mg, from about 100 µg to about 900 µg, from about 100 µg to about 850 µg, from about 100 µg to about 800 µg, from about 100 µg to about 700 µg, from about 100 µg to about 600 µg, from about 100 µg to about 500 µg, from about 100 µg to about 400 µg, from about 100 µg to about 300 µg, from about 100 to about 250 µg, from about 200 µg to about 1.25 mg, from about 200 µg to about 1.0 mg, from about 200 µg to about 900 µg, from about 200 µg to about 850 µg, from about 200 µg to about 800 µg, from about 200 µg to about 700 µg, from about 200 µg to about 600 µg, from about 200 µg to about 500 µg, from about 200 µg to about 400 µg, from about 200 µg to about 300 µg, from about 300 µg to about 1.25 mg, from about 300 µg to about 1.0 mg, from about 300 µg to about 900 µg, from about 300 µg to about 850 µg, from about 300 µg to about 800 µg, from about 300 µg to about 700 µg, from about 300 µg to about 600 µg, from about 300 µg to about 500 µg, from about 300 µg to about 400 µg, from about 400 µg to about 1.25 mg, from about 400 µg to about 1.0 mg, from about 400 µg to about 900 µg, from about 400 µg to about 850 µg, from about 400 µg to about 800 µg, from about 400 µg to about 700 µg, from about 400 µg to about 600 µg, from about 400 µg to about 500 µg, from about 500 µg to about 1.25 mg, from about 500 µg to about 1.0 mg, from about 500 µg to about 900 µg, from about 500 µg to about 850 µg, from about 500 µg to about 800 µg, from about 500 µg to about 700 µg, from about 500 µg to about 600 µg, from about 600 µg to about 1.25 mg, from about 600 µg to about 1.0 mg, from about 600 µg to about 900 µg, from about 600 µg to about 850 µg, from about 600 µg to about 800 µg, or from about 600 µg to about 700 µg.

Other adjuvants that may be used in conjunction with the dengue virus vaccine compositions of the invention, include, but are not limited to, adjuvants containing CpG oligonucleotides, or other molecules acting on toll-like receptors such as TLR4 and TLR9 (for reviews, see, Daubenberger, C. A., Curr. Opin. Mol. Ther. 9(1):45-52 (2007); Duthie et al., Immunological Reviews 239(1): 178-196 (2011); Hedayat et al., Medicinal Research Reviews 32(2): 294-325 (2012)), including lipopolysaccharide, monophosphoryl lipid A, and aminoalkyl glucosaminide 4-phosphates. Additional adjuvants useful in the compositions of the invention include immunostimulatory oligonucleotides (IMO's; see, e.g. U.S. Pat. Nos. 7,713,535 and 7,470,674); T-helper epitopes, lipid-A and derivatives or variants thereof, liposomes, calcium phosphate, cytokines, (e.g. granulocyte macrophage-colony stimulating factor (GM-CSF) IL-2, IFN-α, Flt-3L), CD40, CD28, CD70, IL-12, heat-shock protein (HSP) 90, CD134 (OX40), CD137, CoVaccine HT, non-ionic block copolymers, incomplete Freund's adjuvant, chemokines, cholera toxin; E. coli heat-labile enterotoxin; pertussis toxin; muramyl dipeptide, muramyl peptide analogues, MF59, SAF, immunostimulatory complexes, biodegradable microspheres, polyphosphazene; synthetic polynucleotides.

Additional adjuvants for use with the compositions described herein are adjuvants containing saponins (e.g. QS21), either alone or combined with cholesterol and phospholipid in the characteristic form of an ISCOM ("immune stimulating complex," for review, see Barr and Mitchell, Immunology and Cell Biology 74: 8-25 (1996); and Skene and Sutton, Methods 40: 53-59 (2006)). Such adjuvants are referred to herein as "saponin-based adjuvants". In specific embodiments of the compositions and methods provided herein, the mutant toxins and/or toxin proteins are combined with an ISCOM-type adjuvant or "ISCOM", which is an ISCOM matrix particle adjuvant, such as ISCOMATRIX™, which is manufactured without antigen (ISCOM™ and ISCOMATRIX™ are the registered trademarks of CSL Limited, Parkville, Australia).

Methods of Use

Embodiments of the invention also include one or more of the dengue vaccine compositions described herein (i) for use in, (ii) for use as a medicament or composition for, or (iii) for use in the preparation of a medicament for: (a) therapy (e.g., of the human body); (b) medicine; (c) inhibition of dengue virus replication, including DEN1, DEN2, DEN3 and/or DEN4; (d) induction of an immune response or a protective immune response against one or more of DEN1, DEN2, DEN3 and/or DEN4; (e) induction of a virus neutralizing antibody response against one or more types of dengue (f) treatment or prophylaxis of infection by dengue virus; (g) prevention of recurrence of dengue virus infection; (h) reduction of the progression, onset or severity of pathological symptoms associated with dengue virus infection and/or reduction of the likelihood of a dengue virus infection or, (i) treatment, prophylaxis of, or delay in the onset, severity, or progression of dengue-associated disease(s), including, but not limited to: dengue fever, dengue hemorrhagic fever, dengue shock syndrome. In these uses, the dengue vaccine compositions can optionally be employed in combination with one or more adjuvants (e.g., MAA, aluminum phosphate, Alhydrogel, or other aluminum salt adjuvant, a saponin-based adjuvant such as ISCOMATRIX™ (CSL, Ltd.), a TLR-agonist, or lipid nanoparticles, described herein).

Accordingly, the invention provides methods for the prophylactic and/or therapeutic treatment of dengue virus infection or dengue-associated disease comprising administering one or more of the compositions of the invention to a patient in need of treatment.

A "patient" (alternatively referred to herein as a "subject") refers to a mammal capable of being infected with a dengue virus, such as DEN1, DEN2, DEN3, or DEN4. In preferred embodiments, the patient is a human. A patient can be treated prophylactically or therapeutically. Prophylactic treatment provides sufficient protective immunity to reduce the likelihood or severity of a dengue infection or the effects thereof, e.g., dengue fever. Therapeutic treatment can be performed to reduce the severity or prevent recurrence of a dengue infection or the clinical effects thereof.

Prophylactic treatment can be performed using a dengue virus vaccine composition of the invention, as described herein. The compositions of the invention can be administered to the general population or to those persons at an increased risk of dengue infection, e.g. those persons who live in or will be travelling to areas of the world in which mosquitoes of the genus *Aedes* are prevalent.

Those "in need of treatment" include those already with a dengue infection (e.g. infected with one or more of DEN1, DEN2, DEN3, or DEN4), as well as those prone to have an infection or any person in which a reduction in the likelihood of infection is desired.

Dengue virus vaccine compositions of the invention can be formulated and administered to a patient using techniques well known in the art. Guidelines for pharmaceutical administration in general are provided in, for example, *Vaccines* Eds. Plotkin and Orenstein, W.B. Sanders Company, 1999; *Remington's Pharmaceutical Sciences* 20$^{th}$ *Edition*, Ed. Gennaro, Mack Publishing, 2000; and *Modern Pharmaceutics* 2$^{nd}$ *Edition*, Eds. Banker and Rhodes, Marcel Dekker, Inc., 1990.

Accordingly, the invention provides a method for inducing a protective immune response in a patient against a dengue infection comprising the step of administering to the patient an immunologically effective amount of any of the dengue virus vaccine compositions described herein.

Also provided by the invention is a method for treating dengue infection, or for treating any pathological condition associated with dengue infection, such treatment including prophylaxis of infection, and reduction in the severity of clinical symptoms, delay or prevention of the progression of disease, and/or reduction in the likelihood on infection or the clinical symptoms thereof; the method comprising the step of administering to the patient an immunologically effective amount of any of the vaccine compositions described herein.

Additional embodiments of the invention comprise the administration of two or more compositions of the invention to a patient in a prime/boost regime. Accordingly, the invention relates to a method of preventing or reducing the likelihood of dengue infection in a patient in need thereof, comprising the steps of:

(a) administering a first dengue virus vaccine composition of the invention to the patient;
(b) waiting for a predetermined amount of time to pass after step (a);
(c) administering to the patient a second dengue virus vaccine composition of the invention; and, (d) optionally repeating steps (b) and (c);
whereby the dengue infection is prevented or the likelihood of being infected with dengue is reduced in the patient.

In embodiments of the method above, the dengue virus vaccine compositions of the invention are in the form of a liquid (i.e. the dengue LAV and the non-replicating dengue virus vaccine are formulated together as a liquid in the same vial or container). In alternative embodiments, the dengue virus vaccine compositions are lyophilized (i.e. the dengue LAV and the non-replicating dengue virus vaccine are formulated together and lyophilized in the same vial or other container) and reconstituted with a sterile diluent prior to administration to the patient. In additional embodiments, the LAV and the non-replicating vaccine are provided in separate vials or containers and mixed together prior to administration to the patient. In such embodiments, the LAV and the non-replicating vaccine can be (1) both in the form of a liquid, (2) both lyophilized, or (3) one vaccine in the form of a liquid and one vaccine lyophilized. When one vaccine is in the form of a liquid and one vaccine is lyophilized, the lyophilized vaccine can be reconstituted with the liquid vaccine to form a dengue virus vaccine composition of the invention or the lyophilized vaccine can be reconstituted with a sterile diluent and then mixed with the liquid vaccine to form a dengue virus vaccine composition of the invention.

The amount of time between the first dose and the second dose, or any dose thereafter, is from about 2 weeks to about 2 years. In preferred embodiments of the invention, a time of 2 months to 12 months is allowed to pass between multiple administrations. In alternative embodiments of this aspect of the invention, the amount of time between each administration of each dose of vaccine composition is independently selected from the group consisting of 2 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, and 24 months.

In some embodiments of the invention, the first and second dengue virus vaccine compositions are the same. In alternative embodiments, the first and second dengue virus vaccine compositions are not the same.

The dengue virus vaccine compositions of the invention can be administered by different routes. In preferred embodiments of the invention, the compositions of the invention are administered parenterally, i.e. by intradermal, subcutaneous or intramuscular injection. Subcutaneous and intramuscular administration can be performed using, for example, needles or jet-injectors.

The compositions described herein may be administered in a manner compatible with the dosage formulation, and in such amount as is immunologically-effective to treat and/or reduce the likelihood of dengue infection. The dose administered to a patient, in the context of the present invention, should be sufficient to affect a beneficial response in a patient over time such as a reduction in the level of dengue virus, or to reduce the likelihood of infection by dengue. The quantity of the dengue virus vaccines to be administered may depend on the subject to be treated inclusive of the age, sex, weight and general health condition thereof. In this regard, precise amounts of the vaccine required to be administered will depend on the judgment of the practitioner. In determining the effective amount of the vaccine to be administered in the treatment or prophylaxis against dengue infection, the physician may evaluate circulating plasma levels, progression of disease, and the production of anti-dengue antibodies. In any event, suitable dosages of the immunogenic compositions of the invention may be readily determined by those of skill in the art.

Suitable dosing regimens are preferably determined taking into account factors well known in the art including age, weight, sex and medical condition of the patient; the route of administration; the desired effect; and the particular composition employed. The timing of doses depends upon factors well known in the art, and can range from 2 weeks to 24 months. After the initial administration one or more additional doses may be administered to maintain and/or boost antibody titers.

The invention also relates to methods for preventing dengue infection, or preventing or ameliorating the symptoms thereof, comprising the steps of: (a) mixing a first and a second dengue vaccine to form a dengue virus vaccine composition, wherein the first dengue vaccine is a live, attenuated dengue vaccine and the second dengue vaccine is a non-replicating dengue vaccine; and (b) administering a dose of the dengue virus vaccine composition of step (a) to a patient in which dengue infection or the symptoms thereof are to be prevented or ameliorated. In this method, the dengue virus vaccine composition is administrated to the patient within a time period after mixing in which it remains stable, e.g. within 24 hours. In some embodiments of this aspect of the invention, the non-replicating dengue vaccine is a recombinant dengue subunit vaccine or an inactivated dengue vaccine.

Further embodiments of this aspect of the invention comprise (c) allowing a predetermined amount of time to pass after administration of the dengue virus vaccine composition, and (d) administering a second dose of a composition of the invention. In said embodiments, steps (c) and (d) may optionally be repeated one or more times.

In the method described above the first dengue vaccine is preferably tetravalent and comprises a DEN1, DEN2, DEN3, and DEN 4 component, wherein each component comprises either a live attenuated dengue virus or a live attenuated chimeric flavivirus, as described herein. In exemplary embodiments, the live attenuated vaccine comprises four chimeric flaviviruses; wherein each of the chimeric flavivirus comprises the prM and E proteins of a single dengue virus serotype and the capsid and non-structural proteins of a different flavivirus, wherein the each of the chimeric flavivirus is attenuated. In certain embodiments, the capsid and nonstructural proteins of the four chimeric flaviviruses are from yellow fever virus. In alternative embodiments, the capsid and nonstructural proteins of each of the four chimeric flaviviruses are from a different dengue serotype than the prM and E proteins.

In some embodiments of this aspect of the invention, the second dengue vaccine is a tetravalent recombinant dengue subunit vaccine comprising dengue E proteins, or fragments thereof, from DEN1, DEN2, DEN3, and DEN4. Subunit vaccines useful in this method of the invention are described herein. In preferred embodiments, the E proteins each constitute about 80% of the length of wild type E of DEN1, DEN2, DEN3 and DEN4, starting from amino acid residue 1 at its N-terminus.

In certain embodiments of the method described above, the live, attenuated vaccine is lyophilized and the recombinant subunit vaccine is a liquid prior to mixing. In some embodiments, the mixing of step (a) comprises reconstituting the lyophilized vaccine with the liquid vaccine. In alternative embodiments, the lyophilized vaccine is reconstituted with a sterile diluent prior to mixing with the liquid vaccine in step (a).

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

EXAMPLE 1

Preparation of Formulations for Stability Testing of rYF-DEN2 Chimeric Live Attenuated Virus in Presence of Adjuvants or Dengue Antigens We evaluated the stability of formulations comprising a live attenuated chimeric dengue 2 vaccine ("rYF-DEN2 LAV") in the presence of various adjuvants and/or dengue antigen using an in vitro plaque assay. The LAV used for this study consisted of a dengue/yellow fever ("YF") chimeric virus wherein the prM and E genes of the DEN2 virus were placed on a yellow fever viral backbone to create a YF-DEN2 chimeric virus. The yellow fever-dengue chimeric vaccine vectors were constructed by replacing the genes coding for prM and E proteins from YFV 17D with those of dengue 2. After DNA cloning, RNA was transcribed and transfected into Vero cells to obtain chimeric virus possessing the YFV 17D replication machinery and the external coat of the Dengue 2 virus (see Guirakhoo et al., *J. Virol.* 74(12): 5477-85 (2000)).

All formulations were prepared in a bio-safety cabinet using aseptic technique. Samples for testing were first formulated with the desired adjuvant, dengue antigen, or adjuvant/antigen combination in Dulbecco's PBS and placed in 2 ml sterile ISO vials sealed with 13 mm Flurotec stoppers. Adjuvants/antigens samples tested in this study were as follows: (1) PBS alone; (2) Merck Aluminum Phosphate Adjuvant ("MAPA"); (3) Merck Amorphous Aluminum hydroxyphosphate sulfate adjuvant ("MAA"); (4) DEN2 80% E, amino acids 1-395 of the DEN-2 envelope polypeptide ("DEN2-80E"); (5) ISCOMATRIX™ ("IMX"); (6) a TLR9 agonist adjuvant ("IMO-2055"); (7) DEN2-80E+ MAPA; and (8) DEN2-80E+MAA. Samples containing DEN2-80E with either MAA or MAPA were spun on a table top centrifuge and the supernatant was scanned using a UV spectrophotometer to confirm that DEN2-80E was adsorbed to the aluminum adjuvant. All formulations were stored at 2-8° C. prior to field mixing with rYF-DEN2 LAV.

Adjuvants/antigen samples were field-mixed with rYF-DEN2 LAV in a 1:1 ratio as described below. The dose and concentrations of the samples, prior to and after field-mixing with rYF-DEN2 LAV, were as shown in Table 1.

TABLE 1

Concentration of Monovalent Test Samples

| S. # | Adjuvant/Antigen | Dose (0.5 ml) | Pre-Field Mix Concentration | Post Field Mix Concentration |
|---|---|---|---|---|
| 1 | D-PBS | n/a | n/a | n/a |
| 2 | MAPA | 225 µg | 900 µg/ml | 450 µg/ml |
| 3 | MAA | 225 µg | 900 µg/ml | 450 µg/ml |
| 4 | DEN2-80E | 10 µg | 40 µg/ml | 20 µg/ml |
| 5 | IMX | 60 ISCO ™ units | 240 ISCO ™ units/ml | 120 ISCO ™ units/ml |
| 6 | IMO-2055 | 25 mg | 100 mg/ml | 50 mg/ml |
| 7 | DEN2-80E + MAPA | DEN2-80E- 10 µg MAPA- 225 µg | DEN2-80E- 40 µg/ml MAPA- 900 µg/ml | DEN2-80E- 20 µg/ml MAPA- 450 µg/ml |
| 8 | DEN2-80E + MAA | DEN2-80E- 10 µg MAA- 225 µg | DEN2-80E- 40 µg/ml MAA- 900 µg/ml | DEN2-80E- 20 µg/ml MAA- 450 µg/ml |

1 ml of each of the formulations was prepared.

EXAMPLE 2

Stability Testing of Formulations Comprising rYF-DEN2 Chimeric LAV in Combination with DEN2-80E Antigen and/or Adjuvants Antigen/adjuvant samples listed in Table 1 were field-mixed with rYF-DEN2 LAV and tested for virus viability using an in vitro plaque assay on Vero cells as described below.

Six well plates were seeded with $9 \times 10^5$ Vero cells/well. The passage level of the Vero cells was P31. To dilute viral samples for the plaque assay (T=0 h time point), a 1 mL aliquot of P2 virus from YF-DEN2 LAV (titer $3.3 \times 10^6$ PFU/mL) was thawed in a 22° C. water bath. Dilutions of virus were performed in 2% medium 199 to produce a diluted stock with viral titer of $2 \times 10^5$ PFU/mL. From this diluted stock, 0.5 mL of virus was aliquoted into a fresh tube and mixed with 0.5 mL of one of the adjuvant/antigen formulations described in Example 1 to give a 1:1 dilution. The total volume obtained was 1 mL, of which 0.5 mL was used for the T=0 h plaque assay and 0.5 mL was stored at 4° C. for use in T=24 time point plaque assay.

Further dilutions of the 1:1 LAV:adjuvant/antigen samples were prepared in a 96-well plate to give 1:10, 1:100, 1:1,000, 1:10,000, 1:100,000 and 1:1,000,000 dilutions of each test sample. To perform the assay, Vero cells monolayers were washed with PBS and 200 µl diluted sample (in duplicate) was added to each well of the plates. Virus inoculum was spread onto the cells well and the plates were placed in an incubator. The plates were rocked every 10-15 min for 1 hour to evenly spread the inoculum. After 1 hour of adsorption, cells were overlaid by adding 3 ml of 0.8% methyl cellulose to each well and incubated at 37° C. with 5% $CO_2$.

After 5 days of incubation, the methyl cellulose overlay from each well was aspirated off and 2 mL 1× crystal violet staining solution was added. Staining was carried out for 1 hour at room temperature, at which time the stain was aspirated off. Each well was washed twice with 2 mL of sterile distilled water. Washes were aspirated off into a vacuum container and the plates were allowed to air dry. Virus titer was determined by counting the number of plaques at appropriate virus dilution.

After 24 hours, the procedure above was repeated to determine the viral titer of each sample after storage. Samples were prepared as described above. Results indicate that none of the adjuvants, subunit antigen alone or adjuvant/antigen formulations had any effect on viral titer of the LAV at T=0 (see FIG. 1). The results further indicate that the rYF-DEN2 LAV was stable with subunit antigen alone and most adjuvants even after 24 hours of incubation at 4° C.; however, IMO-2055 caused a significant (~2 log) reduction in virus titer after 24 hours. Cell viability was also lowest in this sample, relative to the other sample groups tested.

EXAMPLE 3

Preparation of Formulations for Stability Testing of rYF-DEN(1-4) Chimeric Live Attenuated Virus in Presence of Adjuvants and/or Dengue Antigens Another study was performed to evaluate the stability of a vaccine comprising live attenuated chimeric yellow fever/dengue virus of dengue types 1-4 ("rYF-DEN (1-4) LAV") in combination with tetravalent DEN-80E (1-4) subunit vaccine, alone or combined with MAA or ISCOMATRIX™ (CSL, Ltd., Parkville, Australia). The Yellow Fever-Dengue chimeric vaccine vectors were constructed by replacing the genes coding for prM and E proteins from YFV 17D with those of each of the four Dengue serotypes. After DNA cloning, RNA was transcribed and transfected into Vero cells to obtain chimeric viruses possessing the YFV 17D replication machinery and the external coat of the relevant Dengue virus.

All formulations were prepared in a bio-safety cabinet using aseptic technique. Samples for testing were formulated with the desired adjuvant, dengue antigen(s), or adjuvant/antigen(s) combination in Dulbecco's PBS and placed in 2 ml sterile ISO vials sealed with Flurotec stoppers. Adjuvants/antigens samples tested in this study were as follows: (1) PBS alone; (2) tetravalent DEN-80E (DEN1-80E+DEN2-80E+DEN3-80E+DEN4-80E); (3) tetravalent DEN-80E+ISCOMATRIX™; (4) tetravalent DEN-80E+MAA. Adjuvants/antigen samples were field-mixed with YF-DEN (1-4) LAV in a 1:1 ratio as described below. The dose and concentrations of the samples, prior to and after field mixing with YF-DEN (1-4) LAV were as shown in Table 2.

TABLE 2

Concentration of Tetravalent Test Samples

| S. # | Adjuvant/Antigen | Dose (0.5 ml) | Pre Field Mix Concentration | Post Field Mix Concentration |
|---|---|---|---|---|
| 1 | D-PBS | n/a | n/a | n/a |
| 2 | tetravalent DEN-80E | DEN1-80E- 10 μg<br>DEN2-80E- 10 μg<br>DEN3-80E- 10 μg<br>DEN4-80E- 20 μg | 200 μg/ml DEN-80E (1-4) | 100 μg/ml DEN-80E (1-4) |
| 3 | tetravalent DEN-80E + IMX | DEN1-80E- 10 μg<br>DEN2-80E- 10 μg<br>DEN3-80E- 10 μg<br>DEN4-80E- 20 μg<br>IMX- 60 ISCO | 200 μg/ml DEN-80E (1-4)<br>240 ISCO units/ml | 100 μg/ml DEN-80E (1-4)<br>120 ISCO units/ml |
| 4 | tetravalent DEN-80E + MAA | DEN1-80E- 10 μg<br>DEN2-80E- 10 μg<br>DEN3-80E- 10 μg<br>DEN4-80E- 20 μg<br>MAA- 225 μg | 200 μg/ml DEN-80E (1-4)<br>900 μg/ml MAA | 100 μg/ml DEN-80E (1-4)<br>450 μg/ml MAA |

All formulations were stored at 2-8° C. prior to field mixing with LAV.

EXAMPLE 4

Stability Testing of Formulations with Live Attenuated YF-DEN (1-4) Virus

Antigen/adjuvant samples prepared in Example 3 were field mixed with rYF-DEN(1-4) LAV and tested for virus viability using an in vitro plaque assay on Vero cells as described below.

Six well plates were seeded with $9\times10^5$ cells/well. The passage level of the Vero cells was P37. Preparation of viruses and 1:1 mixtures of rYF-DEN (1-4) LAV+adjuvant/DEN-80E subunit samples were essentially as described in Example 2 for the monovalent study. Further dilutions of the 1:1 LAV:adjuvant/antigen samples were prepared in a 96-well plate to give 1:10, 1:100, 1:1,000, 1:10,000, 1:100,000 and 1:1,000,000 dilutions of each test sample. The plaque assay, which was performed on samples at T=0 and T=24 hours, was essentially as described in Example 2.

Results indicate that all formulations tested did not appear to have an impact on virus viability (see FIG. 2). However, there was a small (~one log) reduction of rYF-DEN1 virus titer following 24 hours incubation in the samples comprising tetravalent DEN-80E, tetravalent DEN-80E+ISCOMATRIX™ and tetravalent DEN-80E +MAA.

EXAMPLE 5

Preparation of Formulations for Compatibility/Stability Testing of Other Dengue Viruses in the Presence of Adjuvants and/or Dengue Antigens (Tetravalent DEN-80E)

Another study was performed to evaluate the compatibility/stability of other dengue viruses (DENV 1 to 4) when co-formulated in combination with a tetravalent DEN-80E (1-4) subunit vaccine, alone or combined with MAA or Alhydrogel. The wild type (wt) dengue viruses used were the WHO reference strains (DEN1—West Pacific 74; DEN2—16803; DEN3—CH53489; and DEN4—TVP-360).

All formulations were prepared in a bio-safety cabinet using aseptic technique. Samples for testing were formulated with the desired adjuvant, dengue antigen(s), or adjuvant/antigen(s) combination in Dulbecco's PBS and placed in 2 ml sterile ISO vials sealed with Flurotec stoppers. Adjuvants/antigens samples tested in this study were as follows: (1) PBS alone; (2) tetravalent DEN-80E (V180; DEN1-80E+DEN2-80E+DEN3-80E+DEN4-80E); (3) tetravalent DEN-80E (V180)+MAA; and (4) tetravalent DEN-80E (V180)+Alhydrogel. Adjuvants/antigen samples (1)-(4) were separately field-mixed with the wt Dengue viruses in a 1:1 ratio as described below. The dose and concentrations of the samples, prior to and after field mixing with the wt Dengue viruses were as shown in Table 3.

TABLE 3

| Concentration of Tetravalent Test Samples | | | | |
|---|---|---|---|---|
| S. # | Adjuvant/Antigen | Dose (0.5 ml) | Pre Field Mix Concentration | Post Field Mix Concentration |
| 1 | D-PBS | N/A | N/A | N/A |
| 2 | tetravalent DEN-80E (V180) | DEN1-80E- 10 μg<br>DEN2-80E- 10 μg<br>DEN3-80E- 10 μg<br>DEN4-80E- 20 μg | 200 μg/ml DEN-80E (1-4) | 100 μg/ml DEN-80E (1-4) |
| 3 | tetravalent DEN-80E (V180) + MAA | DEN1-80E- 10 μg<br>DEN2-80E- 10 μg<br>DEN3-80E- 10 μg<br>DEN4-80E- 20 μg<br>MAA- 225 μg | 200 μg/ml DEN-80E (1-4)<br>900 μg/ml MAA | 100 μg/ml DEN-80E (1-4)<br>450 μg/ml MAA |
| 4 | tetravalent DEN-80E (V180) + Alhydrogel | DEN1-80E- 10 μg<br>DEN2-80E- 10 μg<br>DEN3-80E- 10 μg<br>DEN4-80E- 20 μg<br>Alhydrogel- 225 μg | 200 μg/ml DEN-80E (1-4)<br>900 μg/ml Alhydrogel | 100 μg/ml DEN-80E (1-4)<br>450 μg/ml Alhydrogel |

All formulations were stored at 2-8° C. prior to field mixing with LAV.

EXAMPLE 6

Compatibility/Stability Testing of Co-Formulations with Wild Type Dengue Viruses in Presence of Adjuvants and/or Dengue Antigens (Tetravalent DEN-80E (V180))

Antigen/adjuvant samples (1)-(4) prepared in Example 5 were field mixed with wt Dengue viruses and tested for virus viability using an in vitro plaque assay on Vero cells as described below.

Vero cells (p38) were seeded into 24-well plates @ $4.0 \times 10^5$ cells per well. Preparation of viruses and 1:1 mixtures of wt dengue viruses+adjuvant/DEN-80E subunit (V180) samples were essentially as described in Example 2 for the monovalent study. Further dilutions of the 1:1 wt dengue virus/antigen samples were prepared in a 96-well plate to give 1:10, 1:100, 1:1,000, 1:10,000, 1:100,000 and 1:1,000,000 dilutions of each test sample. The plaque assay, which was performed on samples at T=0 and T=24 hours, was essentially as described in Example 2.

Figure 3:
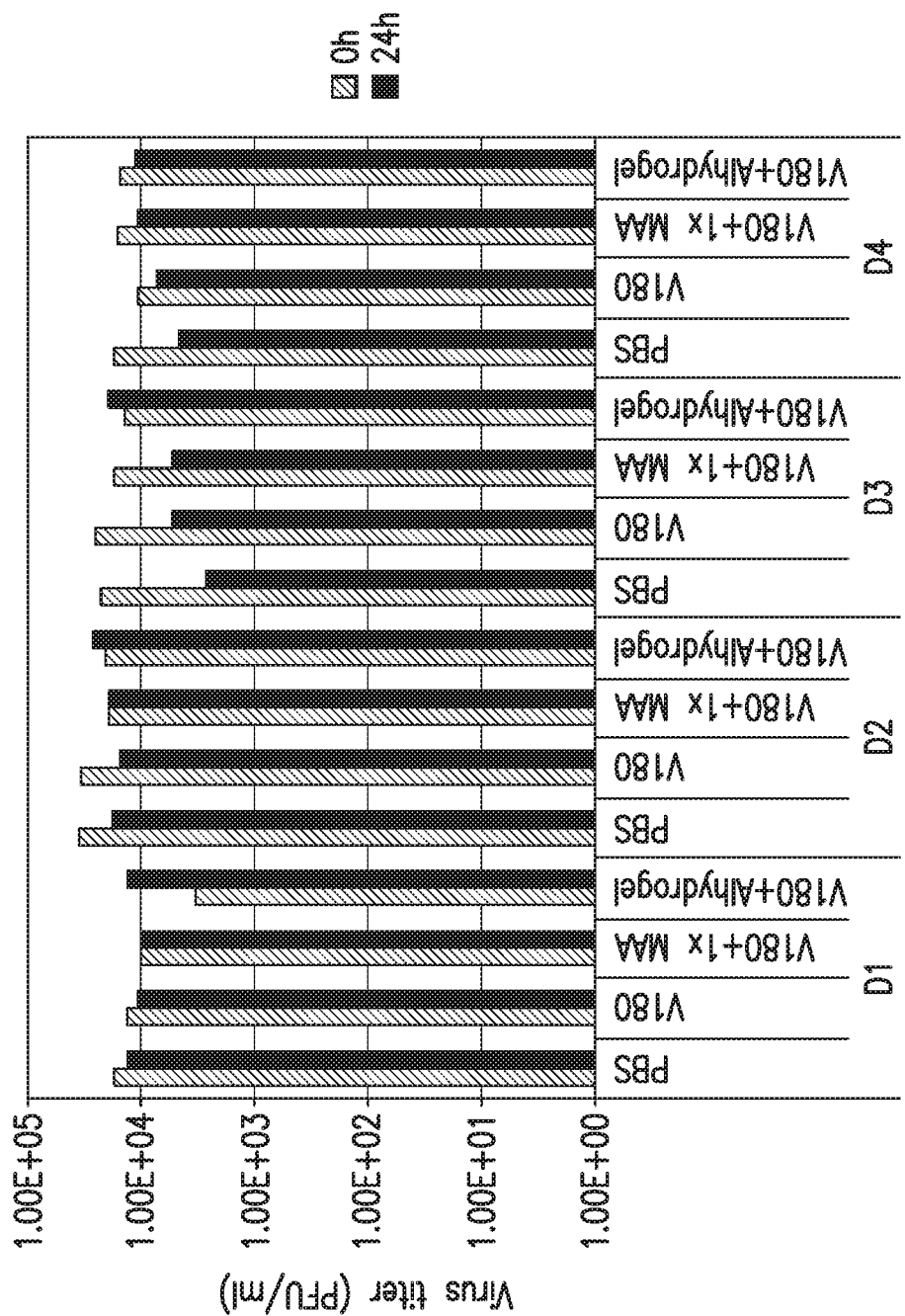

Results indicate that all formulations described did not appear to have an impact on virus viability (see FIG. 3).

However, there was a small (one log) reduction in the DENV 3 titer following 24 hours incubation in the samples comprising PBS, tetravalent DEN-80E and tetravalent DEN-80E+MAA.

EXAMPLE 7

Preparation of Formulations for Compatibility/Stability Testing of rYF-DEN2 Chimeric Live Attenuated Virus in Presence of Adjuvants and/or Dengue Antigens (Whole Inactivated rYF-DEN2)

Another study was performed to evaluate the stability of the rYF-DEN2 LAV in combination with whole purified inactivated rYF-DEN2 (Hy), alone or combined with MAA or Alhydrogel. The purified inactivated rYF-DEN2 virus (PIV) was prepared according to the methods described by Putnak et al., (J Infect Dis. 174(6):1176-84 (1996)). Briefly, supernatants from rYF-DEN2-infected Vero cells were harvested, clarified at 1000 rpm for 10 minutes, filtered through a 0.45 µm filter (CN/CA type) and then subjected to tangential flow filtration (low protein binding 100 kDa cutoff membrane) with a filtration rate of 100 ml/min, pressure 15-20 psi. Following concentration, samples were subjected to sucrose gradient (15-60%) ultra-centrifugation at 4° C. for 18 hours @ 17K rpm. Fractions (1 ml each) were collected from the bottom of the gradient tubes and analyzed for total protein and for Dengue specific protein. Positive fractions were pooled and diluted with PBS and filtered through a 0.22 µm low protein-binding filter (GV type, Millipore). The filtered pool was inactivated with 0.05% formalin, in a 50 ml polypropylene tube at 22° C. in a constant-temperature water bath for 10 days. Complete virus inactivation was confirmed by plaque assay. After inactivation, the solution was filtered through a 0.22 µm filter and, free formalin was neutralized with sodium bisulfate.

All PIV formulations were prepared in a bio-safety cabinet using aseptic technique. Samples for testing were formulated with the desired adjuvant, dengue antigen(s), or adjuvant/antigen(s) combination in Dulbecco's PBS and placed in 2 ml sterile ISO vials sealed with Flurotec stoppers. Adjuvants/antigens samples tested in this study were as follows: (1) PBS alone; (2) whole inactivated rYF-DEN2 PIV; (3) whole inactivated rYF-DEN2 PIV+MAA; and (4) whole inactivated rYF-DEN2 PIV+Alhydrogel. Adjuvants/antigen samples were field-mixed with the rYF-DEN LAV in a 1:1 ratio as described below. The dose and concentrations of the samples, prior to and after field mixing with the rYF-DEN2 live attenuated dengue virus were as shown in Table 4.

TABLE 4

Concentration of Test Samples

| S. # | Adjuvant/Antigen | Dose (0.5 ml) | Pre Field Mix Concentration | Post Field Mix Concentration |
|---|---|---|---|---|
| 1 | D-PBS | N/A | N/A | N/A |
| 2 | whole inactivated rYF-DEN2 PIV | whole inactivated rYF-DEN2- 10 µg | 40 µg/ml whole inactivated rYF-DEN2 | 20 µg/ml whole inactivated rYF-DEN2 |
| 3 | whole inactivated rYF-DEN2 PIV + MAA | whole inactivated rYF-DEN2- 10 µg MAA- 225 µg | 40 µg/ml whole inactivated rYF-DEN2 900 µg/ml MAA | 20 µg/ml whole inactivated rYF-DEN2450 µg/ml MAA |
| 4 | whole inactivated rYF-DEN2 PIV + Alhydrogel | whole inactivated rYF-DEN2- 10 µg Alhydrogel- 225 µg | 40 µg/ml whole inactivated rYF-DEN2 900 µg/ml Alhydrogel | 20 µg/ml whole inactivated rYF-DEN2 450 µg/ml Alhydrogel |

All formulations were stored at 2-8° C. prior to field mixing with LAV.

EXAMPLE 8

Compatibility/Stability Testing of Formulations with rYF-DEN2 Chimeric Live Attenuated Virus in the Presence of Adjuvants and/or Dengue Antigens (Whole Inactivated rYF-DEN2).

Antigen/adjuvant samples prepared in Example 7 were field mixed with rYF-DEN2 LAV to prepare the co-formulation and tested for virus viability using an in vitro plaque assay on Vero cells as described below.

Vero cells (p40) were seeded into 24-well plates @ $4.0 \times 10^5$ cells per well. Preparation of viruses and 1:1 mixtures of rYF-DEN2+adjuvant/whole inactivated YF-DEN2 samples were essentially as described in Example 2 for the monovalent study. Further dilutions of the 1:1 rYF-DEN2 LAV/antigen samples were prepared in a 96-well plate to give 1:10, 1:100, 1:1,000, 1:10,000, 1:100,000 and 1:1,000, 000 dilutions of each test sample. The plaque assay, which was performed on samples at T=0 and T=24 hours, was essentially as described in Example 2.

Results indicate that all formulations tested did not appear to have an impact on virus viability (see FIG. 4).

EXAMPLE 9

Evaluation of a Dengue Prime-Boost Vaccination Strategies in *Macaca mulatta*

The objective of this non-GLP study conducted in Rhesus macaques was to evaluate the co-formulation "prime-boost"

vaccination strategy and compare it to a conventional prime boost strategy. For the study, 2 vaccine candidates, a tetravalent recombinant dengue subunit vaccine candidate (V180) and a tetravalent dengue live attenuated vaccine (LAV) were administered using different regimens. The tetravalent V180 candidate comprised truncated envelope glycoproteins (DEN-80E) from each of the 4 dengue virus serotypes (Dengue Virus (DENV) 1, DENV2, DENV3, and DENV4). The tetravalent LAV comprised live attenuated chimeric yellow fever/dengue viruses of dengue types 1-4 4 ("YF-DEN"). The Yellow Fever-Dengue chimeric vaccine vectors were constructed by replacing the genes coding for prM and E proteins from YFV 17D with those of each of the four dengue serotypes. After DNA cloning, RNA was transcribed and transfected into Vero cells to obtain chimeric viruses possessing the YFV 17D replication machinery and the external coat of the relevant dengue virus.

Healthy adult, Indian Rhesus macaques of either sex (n=4/group), weighing more than 3 kg, and which were flavivirus (DENV 1, 2, 3 and 4, and WNV) antibody-negative by Neutralization titer (for DENV) and ELISA (for WNV) were utilized in this study. Vaccines were administered as described in Table 5. For the study, Group 1 received the YF-DEN vaccine subcutaneously (SC) at 0 and 24 weeks. Groups 2 and 3 received a conventional prime boost in which the YF-DEN vaccine was given at 0 weeks followed by V180 formulated with MAA at 24 weeks. Group 2 received the YF-DEN vaccine by the standard SC route while Group 3 received the vaccine by the intramuscular (IM) route. This allowed us to evaluate the immunogenicity of the YF-DEN vaccine given IM, which was the same route of administration used for the co-formulations given to Groups 4 and 5. Groups 4 and 5 received co-formulations of the YF-DEN vaccine and V180 at 0 and 24 weeks. In Group 4 MAA was included as an adjuvant and Group 5 ISCOMATRIX™ was included as the adjuvant. All vaccines were administered at 0.5-mL per dose. After vaccination, the animals were observed daily for any changes at the inoculation site or other changes in activity or feeding habits that might indicate an adverse reaction to the vaccine.

Virus-neutralizing activity was determined every 4 weeks through study week 32 using the LiCor-based microneutralization assay. For the LiCor assay, Vero cells were seeded overnight in 100 µl 10% media 199 in flat-bottom 96-well tissue culture plates at $1.5 \times 10^4$ cells/well. In separate 96-well plates, serum samples were serially diluted 2-fold in duplicate for 8 dilutions beginning at 1:10. For samples that failed to reach an end-point titration, the sample was retested beginning at a higher dilution. Serum was incubated with an equal volume of virus diluted to 50 pfu/well. All assay dilutions were performed in 2% media 199. The mixture was incubated at 37° C.+5% $CO_2$ for 1 hour. Following neutralization, the entire mixture was added onto the plated Vero cells and incubated for 4 days at 37° C.+5% $CO_2$. Following removal of culture media, cells were fixed with 3.7% formaldehyde in PBS for 30 minutes. Plates were washed 2 times for 5 minutes each with 200 µl 0.1% Titon X-100/PBS. Plates were stained with 50 µl of 4G2 antibody at 2.8 µg/ml. A biotinylated horse anti-mouse IgG was then added at 7.5 µg/ml followed by a cocktail of IRDye® 800CW (Li-Cor, Inc., Lincoln, Nebr.) Streptavidin (1:1000) and DRAQS (1:10,000). Plates were kept in the dark for this final development. Antibodies and reagents were diluted in Odyssey Block buffer supplemented with 0.2% Tween-20. Plates were washed 3 times between antibody exchanges using 0.1% Tween-20/PBS. Incubation steps were performed for 1 hour at room temperature. Washing and dispensing steps were automated using the BioTek® EL406 plate washer system (BioTek Instruments, Inc, Winooski, Vt.). Plates were air-dried and scanned with an infrared Odyssey® Sa imaging system (Li-Cor Biosciences). Raw data was imported into an Excel processing worksheet. Duplicate wells were averaged and serum end-point neutralization titers were defined as the reciprocal of the highest serum dilution that reduces the 800 nm/700 nm fluorescence integrated intensity ratio greater than 50% when compared to virus control included on each assay plate. Prism® (GraphPad Software, Inc.) was used to plot results. All samples were setup beginning at a 1:10 dilution. If a sample failed to neutralize at this dilution a titer of 1:5 was assigned.

TABLE 5

Schedule and Formulations Used in Rhesus Macaque Immunogenicity Study

| Group | Animal ID | Week 0 | Week 24 |
|---|---|---|---|
| 1 | A10L143<br>A6L066<br>S103<br>07D047 | Tetravalent YF-DEN (10e5 pfu each)<br>Administered SC (0.5 ml) | Tetravalent YF-DEN (10e5 pfu each)<br>Administered SC (0.5 ml) |
| 2 | A6L088<br>T87<br>A10R054<br>07D096 | Tetravalent YF-DEN (10e5 pfu each)<br>Administered SC (0.5 ml) | Tetravalent DEN-80E<br>(10, 10, 10, 20 µg each 80E)/<br>MAA (225 µg)<br>Administered IM (0.5 ml) |
| 3 | A6R018<br>T118<br>S63<br>A6L108 | Tetravalent YF-DEN (10e5 pfu each)<br>Administered IM (0.5 ml) | Tetravalent DEN-80E<br>(10, 10, 10, 20 µg each 80E)/<br>MAA (225 µg)<br>Administered IM (0.5 ml) |
| 4 | A10R047<br>07D041<br>T99<br>A5R043 | Tetravalent YF-DEN (10e5 pfu each)/<br>Tetravalent DEN-80E<br>(10, 10, 10, 20 µg each 80E)/<br>MAA (225 µg)<br>Administered IM (0.5 ml) | Tetravalent YF-DEN (10e5 pfu each)/<br>Tetravalent DEN-80E<br>(10, 10, 10, 20 µg each 80E)/<br>MAA (225 µg)<br>Administered IM (0.5 ml) |
| 5 | A10L144<br>A6L111<br>T116<br>A6R028 | Tetravalent YF-DEN (10e5 pfu each)/<br>Tetravalent DEN-80E<br>(10, 10, 10, 20 µg each 80E)/<br>ISCOMATRIX (30 ISCO units)<br>Administered IM (0.5 ml) | Tetravalent YF-DEN (10e5 pfu each)/<br>Tetravalent DEN-80E<br>(10, 10, 10, 20 µg each 80E)/<br>ISCOMATRIX (30 ISCO units)<br>Administered IM (0.5 ml) |

The geometric mean neutralization titers for DENV1, DENV2, DENV3 and DENV4 for all groups for Week 4 (4 weeks post dose 1) are summarized in FIG. 5. At this time point, virus-neutralizing antibody responses were detected in all immunized animals except for one animal that did not respond to DENY 3 in group 1. Key conclusions from the Week 4 results are:

The tetravalent YF-DEN vaccine given IM, stimulated neutralization titers that were equivalent if not better than those induced when the vaccine was given by the standard SC route (compare Group 3 with Groups 1 and or 2).

The neutralization responses measured in the co-formulation groups (Groups 4 and 5) at four weeks post dose 1 were equivalent if not better than those induced when the YF-DEN vaccine was given alone (Groups 1, 2, and 3). This indicates that the co-formulation of the YF-DEN vaccine with the V180 subunit vaccine and adjuvants (MAA or ISCOMATRIX™) does not negatively impact the response to the LAV in the first dose of vaccine.

The geometric mean neutralization titers for DENV1, DENV2, DENV3 and DENV4 for all groups for Week 28 (4 weeks post dose 2) are summarized in FIG. 6. At this time point, virus-neutralizing antibody responses were detected in all immunized animals. Key conclusions from the Week 28 results are:

Both the conventional prime boost (Groups 2 and 3) and the co-formulation prime boost approaches (Group 4 and 5) induced superior neutralization titers to all four DENV types compared to the tetravalent YF-DEN vaccine (Group 1). Titers ranged from 3 to 19 fold higher depending on the DENV type.

The neutralization responses measured in the co-formulation groups (Groups 4 and 5) at four weeks post dose 2 were equivalent to those induced in the groups receiving the conventional prime-boost regimen (groups 2 and 3). This indicates that the co-formulation of the YF-DEN vaccine with the V180 subunit vaccine and adjuvants (MAA or ISCOMATRIX®) does not negatively impact the response to the subunit boost.

The longitudinal geometric mean neutralization titers for DENV1, DENV2, DENV3 and DENV4 for all groups are shown in FIG. 7. Overall, the data demonstrate that the co-formulation prime-boost regimen, wherein animals were administered the V180 subunit vaccine mixed together with a tetravalent LAV at weeks 0 and 24, elicits responses that are comparable to the conventional prime-boost approach and that the responses are superior to the LAV given as a homologous vaccine.

What is claimed is:

1. A dengue virus immunogenic composition comprising a first and a second dengue composition and an adjuvant, wherein the first dengue composition is a tetravalent live, attenuated dengue immunogenic composition and the second dengue composition is a tetravalent non-replicating dengue immunogenic composition; wherein the live attenuated dengue immunogenic composition comprises at least one live, attenuated dengue virus or at least one live attenuated chimeric flavivirus, and wherein the tetravalent non-replicating dengue immunogenic composition comprises dengue E protein, or fragment thereof, from dengue virus type 1 (DEN1), dengue virus type 2 (DEN2), dengue virus type 3 (DEN3), and dengue virus type 4 (DEN4).

2. The composition of claim 1, wherein the non-replicating dengue immunogenic composition is a recombinant dengue subunit immunogenic composition vaccine or an inactivated dengue immunogenic composition.

3. The composition of claim 1, wherein the E proteins each constitute about 80% of the length of wild type E of DEN1, DEN2, DEN3 and DEN4, starting from amino acid residue 1 at its N-terminus.

4. The composition of claim 1, wherein the adjuvant is an aluminum salt adjuvant.

5. The composition of claim 1, wherein the amount of each E protein in the composition is from about 0.5 μg to about 500 μg.

6. The composition of claim 5, wherein the amount of DEN4 E protein is about 1.5 to about 2.5 times the amount of DEN1, DEN2, and DEN3 E proteins.

7. The composition of claim 5, wherein each E protein is recombinantly produced and expressed in insect host cells.

8. The composition of claim 1, wherein the live attenuated dengue composition comprises four chimeric flaviviruses; wherein each chimeric flavivirus comprises the prM and E proteins of a single dengue virus serotype and the capsid and non-structural proteins of a different flavivirus, wherein each of the chimeric flaviviruses are attenuated.

9. The composition of claim 8, wherein the capsid and nonstructural proteins of the four chimeric flaviviruses are from yellow fever virus.

10. The composition of claim 8, wherein the capsid and nonstructural proteins of each of the four chimeric flaviviruses are from a different dengue serotype than the prM and E proteins.

11. The composition of claim 1, wherein the potency of the live attenuated dengue immunogenic composition is from 10 to about $1 \times 10^7$ plaque forming units (PFU's).

12. The composition of claim 11, wherein the potency of the live attenuated dengue vaccine is from about $1 \times 10^3$ to about $1 \times 10^5$ PFU's.

13. A method of inducing an immune response against dengue in a patient in need thereof, comprising administering to the patient an effective amount of a dengue virus immunogenic composition comprising a first and a second dengue composition and an adjuvant, wherein the first dengue composition is a tetravalent live, attenuated dengue immunogenic composition and the second dengue composition is a tetravalent non-replicating dengue immunogenic composition; wherein the live attenuated dengue immunogenic composition comprises at least one live, attenuated dengue virus or at least one live attenuated chimeric flavivirus and wherein the tetravalent non-replicating dengue immunogenic composition comprises dengue E protein, or fragment thereof, from dengue virus type 1 (DEN1), dengue virus type 2 (DEN2), dengue virus type 3 (DEN3), and dengue virus type 4 (DEN4).

14. A method of reducing the likelihood of dengue infection in a patient in need thereof, comprising administering to the patient an effective amount of a dengue virus immunogenic composition comprising a first and a second dengue composition and an adjuvant, wherein the first dengue composition is a tetravalent live, attenuated dengue immunogenic composition and the second dengue composition is a tetravalent non-replicating dengue immunogenic composition; wherein the live attenuated dengue immunogenic composition comprises at least one live, attenuated dengue virus or at least one live attenuated chimeric and wherein the tetravalent non-replicating dengue immunogenic composition comprises dengue E protein, or fragment thereof, from dengue virus type 1 (DEN1), dengue virus type 2 (DEN2), dengue virus type 3 (DEN3), and dengue virus type 4 (DEN4).

15. The method of claim 14, further comprising (a) waiting a predetermined amount of time to pass after the dengue virus immunogenic composition is administered to the patient; and (b) administering to the patient the dengue virus immunogenic composition; whereby the likelihood of being infected with dengue is reduced in the patient.

16. The method of claim 15, wherein the amount of time in step (a) is from 2 months to 2 years.

17. The composition of claim 1, wherein the virus titer of the tetravalent live, attenuated dengue immunogenic composition is not impacted by the addition of the tetravalent non-replicating dengue immunogenic composition.

18. The composition of claim 1, wherein the presence of the non-replicating dengue immunogenic composition does not impact the viability of the tetravalent live, attenuated dengue immunogenic composition.

* * * * *